US00RE44024E

(19) United States
(12) Reissued Patent
Press et al.

(10) Patent Number: US RE44,024 E
(45) Date of Reissued Patent: Feb. 19, 2013

(54) ISOLATION AND CHARACTERIZATION OF ECA1, A GENE OVEREXPRESSED IN ENDOMETROID CARCINOMAS OF OVARY AND ENDOMETRIUM

(75) Inventors: Michael F. Press, Redondo Beach, CA (US); Bahman Saffari, Yorba Linda, CA (US)

(73) Assignee: The University of Southern California, Los Angeles, CA (US)

(21) Appl. No.: 12/779,699

(22) Filed: May 13, 2010

Related U.S. Patent Documents

Reissue of:
(64) Patent No.: 7,371,840
Issued: May 13, 2008
Appl. No.: 10/339,738
Filed: Jan. 8, 2003

(51) Int. Cl.
*C07H 21/04* (2006.01)
*A61K 39/00* (2006.01)

(52) U.S. Cl. ..... 530/387.9; 435/320.1; 435/328; 435/331; 435/372; 530/350; 530/387.3; 530/391.3; 536/23.5; 424/185.1; 424/192.1

(58) Field of Classification Search ..... 536/23.5; 435/320.1, 325, 331, 372; 530/350, 387.3, 530/387.9, 391.3; 424/185.1, 192.1
See application file for complete search history.

(56) References Cited

U.S. PATENT DOCUMENTS

| | | | | |
|---|---|---|---|---|
| 5,166,320 | A | 11/1992 | Wu et al. | |
| 5,264,423 | A | 11/1993 | Cohen et al. | |
| 5,591,721 | A | 1/1997 | Agrawal et al. | |
| 5,635,383 | A | 6/1997 | Wu et al. | |
| 5,652,355 | A | 7/1997 | Metelev et al. | |
| 5,652,356 | A | 7/1997 | Agrawal | |
| 2001/0053519 | A1* | 12/2001 | Fodor et al. | 435/6 |
| 2004/0180339 | A1* | 9/2004 | Press et al. | 435/6 |

OTHER PUBLICATIONS

Burgess et al. (Journal of Cell Biology 1990; 111: 2129-2138).*
Lazar et al. (Molecular and Cellular Biology, 1988, 8: 1247-1252).*
Verma et al. (Nature 1997, 389: 239-242).*
Amalfitano et al.(Current Gene Therapy 2002, 2: 111-133).*
Pandha et al. (Current Opinion in Investigational Drugs 2000; 1 (1): 122-134).*
Boehringer Mannheim Biochemicals, 1994 Catalog (No. 1034731/1006 924), p. 93.*
Genbank Accession No. AB062438; Version AB062438.1 GI:21104461; May 22, 2002; pp. 1-2.*
Skolnick et al. (Trends in Biotechnology 2000; 18: 34-39).*
De Plaen et al. (Immunogenetics, 1994; 40: 360-369).*
Bagnato, A., et al. , "Activation of Mitogenic Signaling by Endothelin 1 in Ovarian Carcinoma Cells" (1997) *Cancer Research* 57:1306-1311.
Cadigan, K.M., et al., "Wnt signaling: a common theme in animal development" (1997) *Genes & Development* 11:3286-3305.
Caduff, R.R., et al., "Mutations of the Ki-ras Oncogene in Carcinoma of the Endometrium" (1995) *Am. J. of Pathology* 146(1) 182-188.
Cheng, J. O., et al., "*AKT2,* a putative oncogene encoding a member of a subfamily of protein-serine/threonine kinases, is amplified in human ovarian carcinomas" (1992) *Proc. Natl. Acad. Sci.* 89:9267-9271.
Clevers, H., et al., "TCF/LEF factors earn their wings" (1997) *TIG* 13(12):485-489.
Connor, P., et al., "Epidermal Growth Factor Activates Protein Kinase C in the Human Endometrial Cancer Cell Line HEC-1-A" (1997) *Gynecologic Oncology* 67:46-50.
Crawford, H. C., et al., "The metalloproteinase matrilysin is a target of β-catenin transactivation in intestinal tumors" (1999) *Oncogene* 18:2883-2891.
Enomoto, T., et al., "K-*ras* Activation Occurs Frequently in Mucinous Adenocarcinomas and Rarely in Other Common Epithelial Tumors of the Human Ovary" (1991) *Am. J. of Pathology* 139(4):777-785.
Enomoto, T., et al., "K-*ras* Activation in Neoplasms of the Human Female Reproductive Tract" (1990) *Cancer Research* 50:6139-6145.
Fujita, M., et al., "Microsatellite Instability and Alterations in the *hMSH2* Gene in Human Ovarian Cancer" (1995) *Int. J. Cancer* (*Pred. Oncol*) 64:361-366.
Fukuchi, T., et al., "β-Catenin Mutation in Carcinoma of the Uterine Endometrium" (1998) *Cancer Research* 58:3526-3528.
Gerlitz, O., et al., "Wingful, an extracellular feedback inhibitor of Wingless" (2002) *Genes & Development* 16:1055-1059.
Giraldez, A.J., et al., "HSPG Modification by the Secreted Enzyme Notum Shapes the Wingless Morphogen Gradient" (2002) *Developmental Cell* 2:667-676.
Greenlee, R.T., et al., "Cancer Statistics, 2001" (2001) *CA Cancer J. Clin.* 51:15-36.
Heikkila, M., et al., "Wnts and the Female Reproductive System" (2001) *J. of Expermental Zoology* 290:616-623.
Ignar-Throwbridge, D., et al., "Mutations of the Ki-*ras* oncogene in endometrial carcinoma" (1992) *Am. J. of Obstetrics and Gynecology* pp. 227-232.
Ito, K., et al., "K-*ras* Point Mutations in Endometrial Carcinoma: Effect on Outcome Is Dependent on Age of Patient" (1996) *Gynecologic Oncology* 63:238-246.
King, B.L., et al., "Microsatellite instability in ovarian neoplasms" (1995) *British J. of Cancer* 72:376-382.

(Continued)

*Primary Examiner* — Stephen Rawlings
(74) *Attorney, Agent, or Firm* — Bingham McCutchen LLP

(57) ABSTRACT

This invention provides an isolated polynucleotide encoding an ECA1 polypeptide. Also provided is the isolated ECA1 polypeptide Further provided is an antibody that specifically recognizes and binds the ECA1 polypeptide or an epitope thereof. The polynucleotides, antibodies and/or polypeptides of this invention may be components of compositions, host cells and/or gene delivery vehicles, where appropriate. In one aspect, the host cell will produce recombinant ECA1, which is further defined herein. In another aspect, the host cell is an antigen presenting cell such as a dendritic cell, and it will display an antigenic portion of the ECA1 polypeptide on its surface. The polypeptides, proteins and compositions of this invention are useful to aid in the diagnosis of a neoplastic condition of a cell of endometrioid origin. In one aspect, the method comprises detecting the presence of an overexpressed ECA1 proto-oncogene in a sample suspected of containing said cell, wherein said overexpression is indicative of the neoplastic condition of said cell. These neoplastic cells include, but are not limited to ovarian and colon carcinoma cells.

25 Claims, 12 Drawing Sheets

OTHER PUBLICATIONS

Link, C. J., et al., "The Relationship between Borderline Ovarian Tumors and Epithelial Ovarian Carcinoma: Epidemiologic, Pathologic, and Molecular Aspects" (1996) *Cynecologic Oncology* 60:347-354.
Moreno-Bueno, G., et al., "β-Catenin Expression Pattern, β-Catenin Gene Mutations, and Microsatellite Instability in Endometrioid Ovarian Carcinomas and Synchronous Endometrial Carcinomas" (2001) *Diagnostic Molecular Pathology* 10(2):116-122.
Morin, P.J., "β-Catenin signaling and cancer" (1999) *BioEssays* 21:1021-1030.
Nardini, M., et al., "a/β Hydrolase fold enzymes: the family keeps growing" (1999) *Curr. Opin. Struct. Biol.* 9:732-737.
Palaclos, J., et al., "Mutations in the β-Catenin Gene (*CTNNB1*) in Endometrioid Ovarian Carcinomas" (1998) *Cancer Research* 58:1344-1347.
Peifer, M., et al., "The Ballet of Morphogenesis: Unveiling the Hidden Choreographers" (2002) Cell Press 109:271-274.
Saegusa, M., et al. "Frequent nuclear β-Catenin accumulation and associated mutations in endometrioid-type endometrial and ovarian carcinomas with squamous differentiation" (2001) *J. of Pathology* 194:59-67.
Saffari, B., et al. "Amplification and Overexpression of HER02/*neu* (c-erB2) in Endometrial Cancers: Correlation with Overall Survival" (1995) *Cancer Research* 55:5693-5698.
Shtutman, M., et al., "The cyclin D1 gene is a target of the β-Catenin/LEF-1 pathway" (1999) *Proc. Natl. Acad, Sci. USA* 96:5522-5527.
Tong-Chuan, H., et al., "Identification of c-*MYC* as a Target of the APC Pathway" (1998) *Science* 281:1509-1512.
Wu, R., et al., "Diverse Mechanisms of β-Catenin Derugulation in Ovarian Endometrioid Adenocarcinomas" (2001) *Cancer Research* 61:8247-8255.

* cited by examiner

Figure 2A

5′cggccggacagcccgtggagagcttcccgctggacttcacggccgtggagggtaac ATG GAC AGC
TTC ATG GCG CAA GTC AAG AGC CTG GCG CAG TCC CTG TAC CCC TGC TCC GCG CAG
CAG CTC AAC GAG GAC CTG CGC CTG CAC CTC CTA CTC AAC ACC TCG GTG ACC TGC
AAC GAC GGC AGC CCC GCC GGC TAC TAC CTG AAG GAG TCC AGG GGC AGC CGG CGG
TGG CTC CTC TTC CTG GAA GCC GTC TGG TAC TGC TTC AAC CGC GAG AAC TGC GAC
TCC AGA TAC GAC ACC ATG CGG CGC CTC ATG AGC TCC CGG GAC TGG CCG CGC ACT
CGC ACA GGC ACA GGG ATC CTG TCC TCA CAG CCG GAG GAG AAC CCC TAC TGG TGG
AAC GCA AAC ATG GTC TTC ATC CCC TAC TGC TCC AGT GAT GTT TGG AGC GGG GCT
TCA TCC AAG TCT GAG AAG AAC GAG TAC GCC TTC ATG GGC GCC CTC ATC ATC CAG
GAG GTG GTG CGG GAG CTT CTG GGC AGA GGG CTG AGC GGG GCC AAG GTG CTG CTG
CTG GCC GGG AGC AGC GCG GGG GGC ACC GGG GTG CTC CTG AAT GTG GAC CGT GTG
GCT GAG CAG CTG GAG AAG CTG GGC TAC CCA GCC ATC CAG GTG CGA GGC CTG GCT
GAC TCC GGC TGG TTC CTG GAC AAC AAG CAG TAT CGC CAC ACA GAC TGC GTC GAC
ACG ATC ACG TGC GCG CCC ACG GAG GCC ATC CGC CGT GGC ATC AGG TAC TGG AAC
GGG GTG GTC CCG GAG CGC TGC CGA CGC CAG TTC CAG GAG GGC GAG GAG TGG AAC
TGC TTC TTT GGC TAC AAG GTC TAC CCG ACC CTG CGC TGC CCT GTG TTC GTG GTG
CAG TGG CTG TTT GAC GAG GCA CAG CTG ACG GTG GAC AAC GTG CAC CTG ACG GGG
CAG CCG GTG CAG GAG GGC CTG CGG CTG TAC ATC CAG AAC CTC GGC CGC GAG CTG
CGC CAC ACA CTC AAG GAC GTG CCG GCC AGC TTT GCC CCC GCC TGC CTC TCC CAT
GAG ATC ATC ATC CGG AGC CAC TGG ACG GAT GTC CAG GTG AAG GGG ACG TCG CTG
CCC CGA GCA CTG CAC TGC TGG GAC AGG AGC CTC CAT GAC AGC CAC AAG GCC AGC
AAG ACC CCC CTC AAG GGC TGC CCC GTC CAC CTG GTG GAC AGC TGC CCC TGG CCC
CAC TGC AAC CCC TCA TGC CCC ACC GTC CGA GAC CAG TTC ACG GGG CAA GAG ATG
AAC GTG GCC CAG TTC CTC ATG CAC ATG GGC TTC GAC ATG CAG ACG GTG GCC CAG
CCG CAG GGA CTG GAG CCC AGT GAG CTG CTG GGG ATG CTG AGC AAC GGA AGC TAG
gcagactgtctggaggaggagccggcactgaggggcccagacacccgctgcaccagtgccacctcacccca
caccagcaggccctcccgtctcttcgggacagggcaccagccgtcccccctgtctgggtatgctcactgcc
ctcctgccccggctttccctgcccctctcccacagcccagccagagacaagggacctgctgtcatccccat
ctgtggcctgggggtccttcctgacaacgagggggtagccagaagagaagcactggattcctcagtccacc
agctcagacagcacccaccggccccacccatcaagccctttatattattttataaagtgactttttatt
actttaatttttaaaaaaaggaaaataagaatatatgatgaatgatattgttttgtaacttttaaaaat
gattttaaagagacaaaaaaaaaaaaaaaaaaaaaaaaaaaaa

Figure 2B

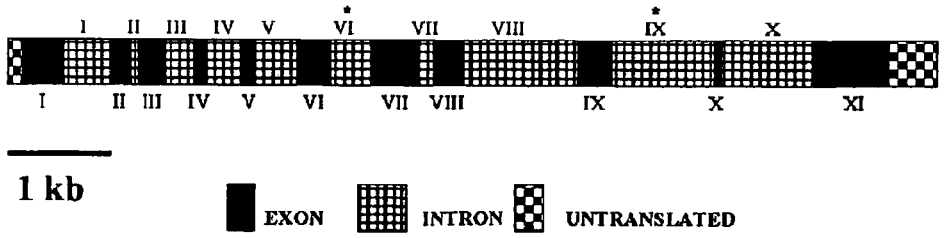

Figure 3

```
  1 MDSFMAQVKSLAQSLYPCSAQQLNEDLRLHLLLNTSVTCNDGSPAGYYLKESRGSRRWLL
 61 FLEAVWYCFNRENCDSRYDTMRRLMSSRDWPRTRTGTGILSSQPEENPYWWNANMVFIPY
121 CSSDVWSGASSKSEKNEYAFMGALIIQEVVRELLGRGLSGAKVLLLAGSSAGGTGVLLNV
181 DRVAEQLEKLGYPAIQVRGLADSGWFLDNKQYRHTDCVDTITCAPTEAIRRGIRYWNGVV
241 PERCRRQFQEGEEWNCFFGYKVYPTLRCPVFVVQWLFDEAQLTVDNVHLTGQPVQEGLRL
301 YIQNLGRELRHTLKDVPASFAPACLSHEIIIRSHWTDVQLKGTSLPRALHCWDRSLHDSH
361 KASKTPLKGCPVHLVDSCPWPHCNPSCPTVRDQFTGQEMNVAQFLMHMGFDMQTVAQPQG
421 LEPSELLGMLSNGS
```

Figure 4A

```
ECA1 32   LLNTSVTCNDGSPAGYYLKESRGSRRWLLFLEAVWYCFNRENCDSRYDTMRRLMSSRDWP
          L-NTS+TCNDGS-AG+YL++---S++W++-LE--W+CF+--+C-SR+--+R-LM+S--WP
Wf   93   LANTSITCNDGSHAGFYLRKHPSSKKWIVLLEGGWHCFDVRSCRSRWMRLRHLMTSSQWP

ECA1 92   RTRTGTGILSSQPEENPYWWNANMVFIPYCSSDVWSGASSKSE----KNEYAFMGALIIQ
          -TR---GILS--PEENPYW-NAN-V-IPYCSSD-WSG--++-+     +N-+-FMGALI++
Wf   153  ETRDVGGILSPHPEENPYWHNANHVLIPYCSSDSWSGTRTEPDTSDRENSWRFMGALILR

ECA1 148  EVVRELL--GRGLSGAKVLLLAGSSAGGTGVLLNVDRVAEQLEKLGYPAIQVRGLADSGW
          +V+-EL+  G-G------L+L-GSSAGG-GV+LN+DR+-+-L-------I-VRG++DSGW
wf   213  QVIAELIPVGLGRVPGGELMLVGSSAGGMGVMLNLDRIRDFLVNEKKLQITVRGVSDSGW

ECA1 206  FLDNKQYRHTDCVDTITCAPTEAIRRGIRYWNGVVPERCRRQFQEGEEWNCFFGYKVYPT
          FLD-+-Y---       --A--EA+R+G-+-W-G++PE-C-+-+---E-W-C++GY++YPT
Wf   273  FLDREPYTPA------AVASNEAVRQGWKLWQGLLPEECTKSYPT-EPWRCYYGYRLYPT

ECA1 266  LRCPVFVVQWLFDEAQLTVDNVHLTGQPVQEGLRLYIQNLGRELRHTLKDVPASFAPACL
          L+-P+FV-QWLFDEAQ+-VDNV   G-PV------YI--+G--LR-+L-+V-A-FAP+C+
Wf   326  LKTPLFVFQWLFDEAQMRVDNV---GAPVTPQQWNYIHEMGGALRSSLDNVSAVFAPSCI

ECA1 326  SHEIIIRSHWTDVQLKGTSLPRALHCWDRSL----HDSHKASKTP
          -H-++-+--W-++++---SLP-AL-CW+-S-    HD--K-S--P
Wf   383  GHGVLFKRDWVNIKIDDISLPSALRCWEHSTRSRRHDKLKRSTEP

ECA1 360  HKASKTPLKGCPVHLVDSCPWPHCNPSCPTVRDQFTGQEMNVAQFLMHMGFDMQTVAQPQ
          H+--+-P-K-C-+-L++-C-WP-CN-SCPT+-+--TG+EM---+-L---G-D++-VA---
wf   589  HRVPRVPEK-CGLRLLERCSWPQCNHSCPTLTNPMTGEEMRFLELLTAFGLDIEAVAAAL

ECA1 420  G--------LEPSELLGMLS
          G         +E-+EL+-ML+
wf   648  GVDMHTLNNMERTELVNMLT
```

Figure 4B

```
ECA1    27  LRLHLLLNTSVTCNDGSPAGYYLKESRGSRRWLLFLEAVWYCFNRENCDSRYDTMRRLMS
            L+---L-N-+VTCNDGS-AG+YL++S-GSRRW++F-E--W+C++-++C-+R+---R-LM+
CP6173  31  LKRVFLSNRTVTCNDGSQAGFYLRKSPGSRRWVVFFEGGWHCYDHKSCRARWLKQRHLMT

ECA1    87  SRDWPRTRTGTGILSSQPEENPYWWNANMVFIPYCSSDVWSGASSKSE-KNEYAFMGALI
            S--WP-TR---G+LS+-P-ENPYW+NAN-VF+PYCSSD-WSG---+-+ ++---FMG+LI
CP6173  91  SVQWPETRDVGGLLSALPSENPYWYNANHVFVPYCSSDSWSGTKVRPDTRDGLRFMGSLI

ECA1   146  IQEVVREL--LGRGLSGAKVLLLAGSSAGGTGVLLNVDRVAEQLEKLGYPAIQVRGLADS
            +++V+-+L  LG-G-S----LL+AGSSAGG-GV+LN+D+V---L+------+-VRG++DS
CP6173 151  VRQVMSDLVPLGLGHSQGADLLMAGSSAGGLGVMLNLDKVRTFLQNERGLKVSVRGVSDS

ECA1   204  GWFLDNKQYRHTDCVDTITCAPTEAIRRGIRYWNGVVPERCRRQFQEGEEWNCFFGYKVY
            GWFLD-+-Y---      --A-+EA+R+G-R-W+G-+PE-C--+--+ E-W-C+FG+++Y
CP6173 211  GWFLDREPYTPG------AVAASEAVRQGWRMWDGALPEACVAEHSK-EPWRCYFGHRLY

ECA1   264  PTLRCPVFVVQWLFDEAQLTVDNVHLTGQPVQEGLRLYIQNLGRELRHTLKDVPASFAPA
            -TL+-P+FV-QWLFDEAQ+--D+V   G-PV------YI-++G--LR-+L-+V-A-FAP+
CP6173 264  NTLKSPLFVFQWLFDEAQMRADSV---GAPVTPQQWDYIHDMGGALRESLNNVSAVFAPS

ECA1   324  CLSHEIIIRSHWTDVQLKGTSLPRALHCWDRSLHDSHKASKTPLKGCPVHL 374
            C+-H-++-+--W--+++---+L--AL-CW++S--D--++----+---P--L
CP6173 321  CIGHSVLTKRDWMKIRIDDITLADALRCWEQSNADERQSQWRSINRSPQKL 371

ECA1   368  KGCPVHLVDSCPWPHCNPSCPTVRDQFTGQEMNVAQFLMHMGFDMQTVAQPQGLEPSELL
            K-C-+-L++-C-WP-CN-SCPT+-+--TG+EM---+-L---G-DM--VA---G++---L-
CP6173 482  KKCALRLLERCSWPQCNHSCPTLTNPLTGEEMKFLELLASFGLDMDAVATALGVDMQTLN

ECA1   428  GM
            -M
CP6173 542  NM
```

Figure 4C

```
ECA1   39   CNDGSPAGYYLKESRGS--RRWLLFLEAVWYCFNRENCDSRYDTMRRLMSSRDWPRTRTG
            C-DGS--GY+--+--GS  --WL+-LE---+C-N--+C-SR--T  RL-SS----+----
PAE    32   CLDGSLPGYHFHKGSGSGANNWLIQLEGGGWCNNIRSCVSRKGT--RLGSSNFMEKELAF

ECA1   97   TGILSSQPEENPYWWNANMVFIPYCSSDVWSGASSKSEKNEYAFMGALIIQEVVRELLGR
            +GILS++--ENP-++N-N-V-+-YC----++G-S-------- F-G--I---V+-ELL-+
PAE    90   SGILSNKASENPDFYNWNRVKVRYCDGASFTGDSEAVAPRLQ-FRGQRIWLAVMDELLAK

ECA1   157  GLSGAKVLLLAGSSAGGTGVLLNVDRVAEQLEKLGYPAIQVRGLADSGWFLDNKQYRHTD
            G+--AK--LL+G-SAGG---+L+-D-----L-     ----V+-L+D+G+FL+---
PAE    149  GMRNAKQALLSGCSAGGLAAILHCDYFRNLLP----RTTTVKCLSDAGYFLNVLD-----

ECA1   217  CVDTITCAPTEAIRRGIRYWNGVV---------PERCRRQFQEGEEWNCFFGYKVYPTLR
                ++--P-  +R    +++GVV          P+-C----+---   CFF---V---++
PAE    200  ----VSGGPR--LR---SFFSGVVTLQGSAKNLPQSCTSHLKPTL---CFFPQNVVSQIK

ECA1   268  CPVFVVQWLFDEAQL
            -P+F+V---+D--Q+
PAE    248  TPLFLVNAAYDSWQI
```

ISOLATION AND CHARACTERIZATION OF ECA1, A GENE OVEREXPRESSED IN ENDOMETROID CARCINOMAS OF OVARY AND ENDOMETRIUM

Matter enclosed in heavy brackets [ ] appears in the original patent but forms no part of this reissue specification; matter printed in italics indicates the additions made by reissue.

STATEMENT OF GOVERNMENT SUPPORT

This application is supported in part by a grant from the U.S. Army Medical Research and Material Command (Grant No. DAMD17-94-J-4234). Accordingly, the United States government may have certain rights in this invention.

BACKGROUND

The following terms are abbreviated as follows within this specification: Endometrioid Carcinoma 1 (ECA1), T Cell Factor (TCF), Lymphocyte Enhancing Factor (LEF), Differential Display Reverse Transcriptase (DDRT), Heparan-Sulfate Proteoglycans (HSPG).

Ovarian cancer is the fifth leading cause of cancer death among women in the United States and has the highest mortality rate of all gynecologic cancers. Greenlee, R. T. et al., Cancer Statistics, 2001. CA: A Cancer Journal for Clinicians 51(1):15-36. The prognosis for survival from ovarian cancer is largely dependent upon the extent of disease at diagnosis. Women diagnosed with local disease are over 3 times more likely to survive 5 years than women with distant disease. However, only one fourth of women present with localized disease at diagnosis. Ries, L. A. et al., (1998), SEER Cancer Statistics Review 1973-1995, Bethesda, Md.: National Cancer Institute.

Ovarian and other gynecological malignancies can be the result of acquired or inherited genetic alterations. Maintenance of a malignant phenotype requires sustained expression of important transforming genetic alterations. Alterations in several genes are described for endometrial and ovarian carcinomas. These alterations include mutations in ras (Enomoto, T. et al. (1990) Cancer Res. 50:6139-6145), β-catenin (Ignar-Trowbridge, D. et al. (1992) Am. J. Obstet. Gynecol. 167:227-232), PTEN (Caduff, R. F. et al. (1995) Am. J. Pathol. 146:182-188), p 53 (Ito, K. et al. (1996) Gynecol. Oncol. 63:238-246), DNA-repair defects manifested as mircosatellite instability (Risinger, et al. (1993) Cancer Res. 53:5100-5103) as well as gene amplification in c-myc (Jasano et al. (1990) Cancer Res. 65:1545-1551) and HER-2/neu (Saffari et al. (1995) Cancer Res. 55:5693-5698.). Some of these genetic alterations are strongly associated with specific histologic types of carcinoma found in either endometrium or ovary (Saegusa et al. (2001) J. Pathol. 194:59-67; Sasano, H. et al. (1990) Cancer Res. 53:5100-5103; and Enomoto, T. et al. (1991) Am. J. Pathol. 139:777-785).

Despite the numerous examples of biomarkers shown to be associated with various cancers, the usefulness of such tools for therapeutic diagnostic, prognostic and other detection applications are limited in that they have been shown to be ineffective, unreliable, lacking in sensitivity and/or predictiveness. Thus, there exists a continuing need to identify antigens, antigenic epitopes and other biomarkers associated with cancer and to develop new materials and kits to aid in the early detection, therapy and monitoring of related cancers.

The present invention satisfies this need for endometrioid carcinomas such as ovarian cancer and provides related advantages as well.

DETAILED DESCRIPTION OF THE INVENTION

A novel gene, ECA1, which is overexpressed in endometrioid carcinomas of ovary and endometrium was isolated. It was found to be a tumor antigen in colon carcinoma. ECA1 is evolutionarily conserved among eukaryotic organisms, expressed in fetal tissues and has a high degree of homology to Drosophila wingful/Notum the putative inhibitor of wingless activity (Giraldez et al. (2002) Dev. Cell 5:667-676 and Gerlitz et al. (2002) Genes and Develop. 16:1055-1059). Based on the reported observation that ectopic expression of constitutively active armadillo (β-catenin counterpart in Drosophila), could induce the expression of wingful/Notum (Giraldez et al. (2002) supra) and the presence of putative TCF/LEF DNA binding consensus sequences in the promoter region of ECA1, ECA1 is a β-catenin/TCF/LEF transcription complex target gene with significant roles in regulation of the Wnt/βcatenin pathway and in development of some human carcinomas.

Thus, this invention provides isolated polynucleotides encoding an ECA1 polypeptide, modifications thereof and active fragments of each. In one aspect, the polynucleotides encode the polypeptide has the sequence shown in SEQ ID NO. 1. In one aspect, the polynucleotide has the sequence shown in FIG. 2. In a further aspect, this polynucleotide has the sequence shown in SEQ ID NO. 2. Further provided are fragments that specifically hybridize to the ECA1 polynucleotide under moderate or stringent hybridization conditions, e.g., for use as probes or primers.

Further provided is the isolated ECA1 polypeptide which has the sequence shown in SEQ ID NO: 1, active fragments thereof and modifications of all. An antibody that specifically recognizes and binds the ECA1 polypeptide or an epitope thereof is also provided. In one aspect, the antibody is a monoclonal antibody. The invention further provides hybridoma cell lines that produce the anti-ECA1 monoclonal antibodies.

The polynucleotides, antibodies and/or polypeptides of this invention are components of compositions, host cells and/or gene delivery vehicles, where appropriate. The polynucleotides, antibodies and/or polypeptides and host cells may be combined with a carrier such as a solid support or with a pharmaceutically acceptable carrier. In one aspect, a host cell produces recombinant ECA1.

In one aspect, the host cell is an antigen presenting cell such as a dendritic cell, and it displays an antigenic portion of the ECA1 polypeptide on its surface.

The polypeptides, proteins and compositions of this invention are useful to aid in the diagnosis or treatment of a neoplastic condition of a cell of endometrioid origin. In one aspect, the diagnostic method comprises detecting the presence of ECA1 proto-oncogene in a sample suspected of containing said ECA1 polynucleotide or polypeptide, wherein said overexpression is indicative of the neoplastic condition of said cell. In another aspect, the is useful to diagnose the predisposition to development of a condition related to ECA1 overexpression or it is useful to monitor the progress of therapy.

This invention also provides a screen for a potential therapeutic agent for the reversal of the neoplastic condition of a cell of endometrioid origin and wherein said cell overexpresses ECA1 proto-oncogene, comprising a contacting a sample with an effective amount of a potential agent and assaying for reversal of the neoplastic condition or determining if the amount of ECA1 expression has been altered by the treatment. Examples of such agents include, but are not limited to agents that inhibit expression of the ECA1 gene such as ribozymes, antisense or small molecules, agents that inhibit the interaction of the ECA1 protein in the β-catenin/TCF pathway and agents that induce or promote an immune response against neoplastic cells expressing the ECA1 protein, e.g., antibodies, peptide vaccines, antigen presenting cells that express the ECA1 protein on their cell surface and immune effector cells raised in the presence and at the expense of this APC.

A kit for use in the diagnostic or therapeutic methods of this invention is further provided. It provides one or more compositions of this invention that are useful in the diagnostic or therapeutic methods, e.g., a polynucleotide that specifically hybridizes with ECA1 mRNA or cDNA, and anti-ECA1 antibody such as a monoclonal antibody.

BRIEF DESCRIPTION OF THE FIGURES

FIG. 2. ECA1 cDNA sequence and genomic structure. FIG. 2A shows ECA1 cDNA sequence (SEQ ID NO. 1). The 5' and 3' untranslated sequences are shown in small letters. The putative initiation and termination codons are shown in bold. The initiation codon predicted by OK/SW-CL.30 is underlined. ECA1 cDNA sequence differs from LOC147111 at codon 340. ECA1 encodes a valine (GTG) whereas LOC147111 encodes a leucine (TTG). The G for T substitution is in bold and underlined. (FIG. 2B) is a schematic diagram illustrating the genomic organization of ECA1. The 5' and 3' untranslated regions are shown as checkered boxes. The exons are shown as black boxes and the introns as square hatched boxes. ECA1 contains 11 exons and 10 introns. "*" Denotes the location of single nucleotide polymorphism in introns 6 and 9.

FIG. 3. The predicted amino acid sequence of ECA1 (SEQ ID NO. 1). ECA1 protein is predicted to contain 434 amino acids with nine CK-2, nine PKC phosphorylation, and a tyrosine kinase phosphorylation sites. The potential phosphorylation sites are shown in bold. The serine or threonine residues harboring both PKC and CK-2 phosphorylation site consensus are also underlined. A 17 amino acids long bipartite nuclear targeting sequence is boxed. There are nine N-myristoylation sites however only the glycine residue at position 42 with the most likely potential for N-myristoylation is underlined. The potential N-glycosylation site on Asn 34 is also boxed.

FIG. 4. ECA1 encodes a protein highly homologous to Notum/wingful protein of fruit fly with structural similarity to pectin acetylesterase. Alignments of ECA1 with wingful/Notum protein (A) (SEQ ID NOs. 8 and 9), hypothetical protein agCP6173 (B) (SEQ ID NOs. 10 and 11) and pectin acetylesterase (C) (SEQ ID NOs. 12 and 13). "+" Indicates sequence similarity; sequence identity is highlighted in bold. The conserved/identical amino acid sequences possibly representing conserved domains between ECA1 and PAE are shown in bold. The G-X-S-X-G (SEQ ID NO.: 7) consensus active site motif of α/β hydrolase enzymes is boxed in A and C. 'X' may represent any amino acids and G represent glycine or any small amino acid.

MODES FOR CARRYING OUT THE INVENTION

Figure 1:
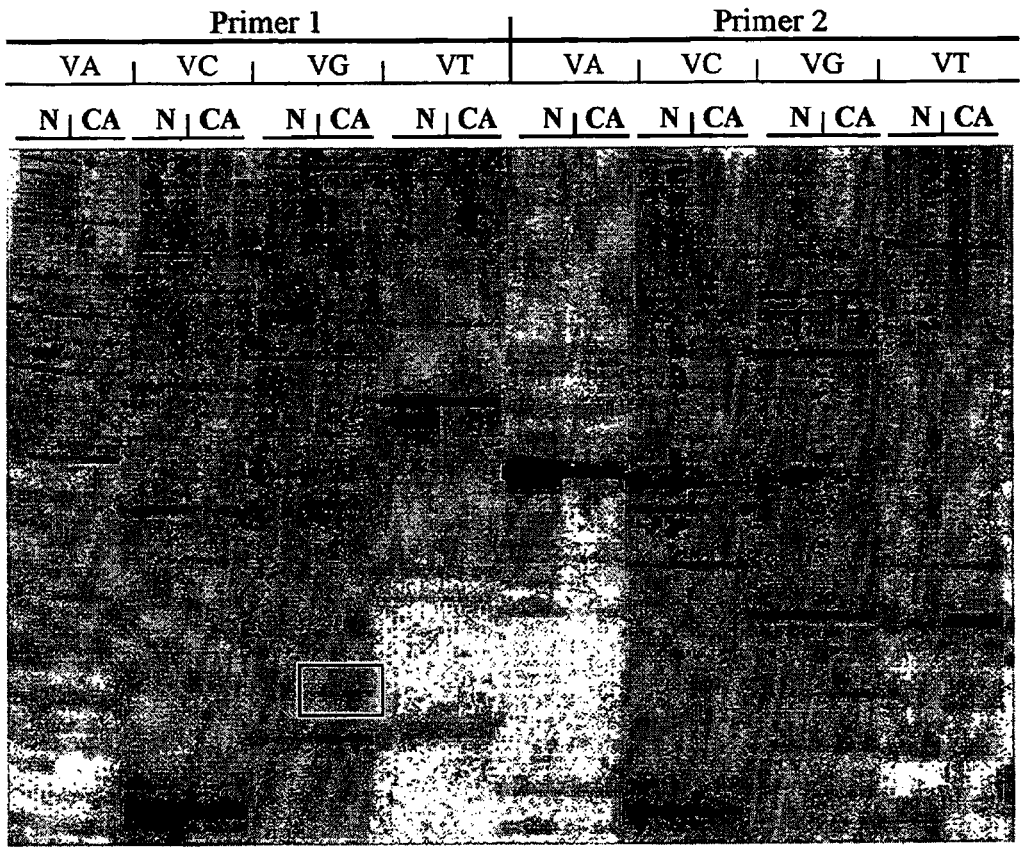
FIG. 1. Differential display of mRNA from human proliferative endometrium (N) and endometrial carcinoma (CA). The radiolabeled cDNA species amplified with the primer pair (dT)12VG and decamer OP-DDRT1 were resolved by polyacrylamide gel electrophoresis. ECA1 partial cDNA is solely displayed in endometrial carcinoma (enclosed in a box).
Figure 5:
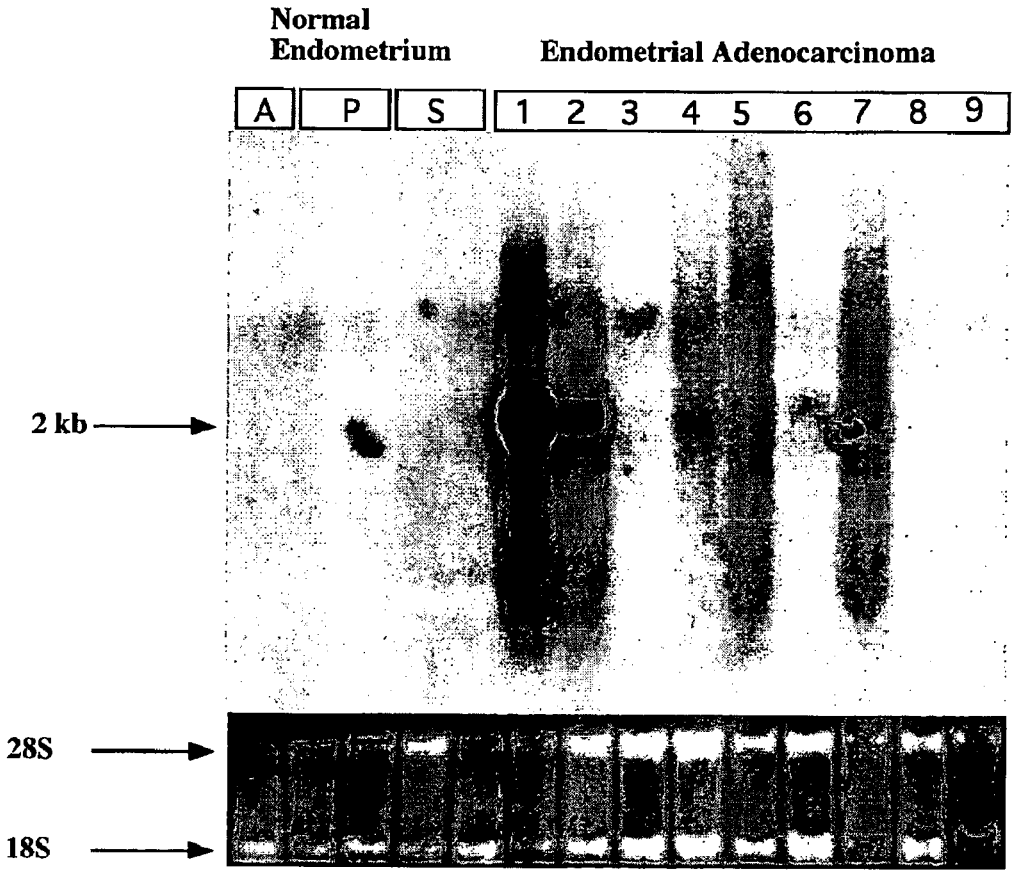
FIG. 5. Expression of ECA1 in endometrial carcinomas. Total RNA (10 μg per lane) from endometrial carcinomas and normal endometria were examined for expression of ECA1 by Northern blot analysis using a DDRT-derived partial ECA1 cDNA as a probe under stringent hybridization conditions. An approximately 2 kb ECA1 mRNA was identified in 5 endometrial carcinomas. Three cases show low levels (lanes 4, 5, and 7), one case shows moderate level (lane 2) and one case shows high levels (lane 1) of ECA1 expression. ECA1 mRNA was not detected in atrophic postmenopausal endometrium (A), normal proliferative phase endometrium (P), and normal secretory phase endometrium (5). Ethidium bromide-stained 28S and 18S ribosomal RNAs are also shown (bottom panel).
Figure 6:
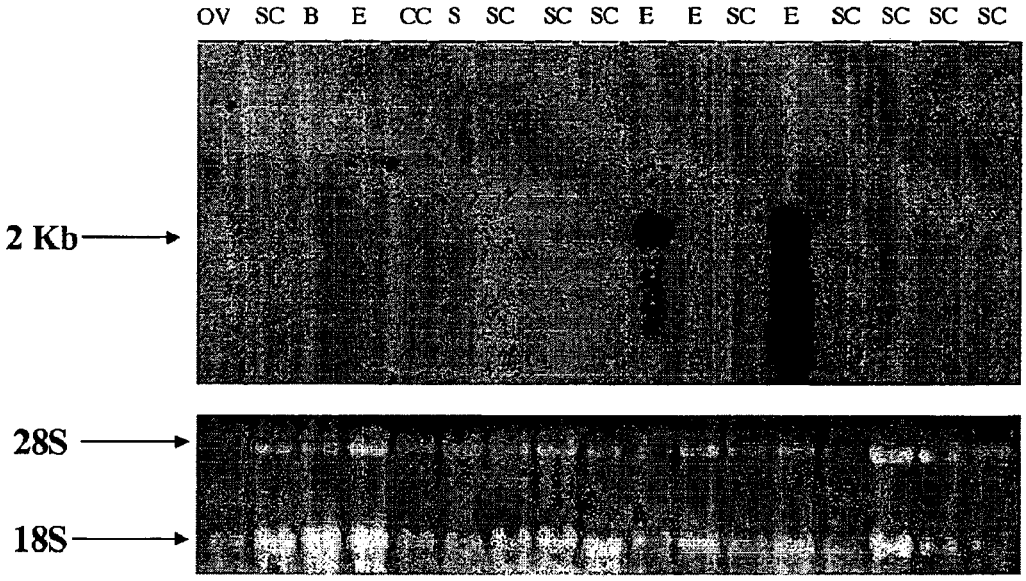
FIG. 6. Expression of ECA1 in ovarian tumors. Total RNA (10 μg per lane) from ovarian tumors and normal ovary were examined for expression of ECA1 by Northern blot analysis using a partial ECA1 cDNA as a probe under stringent hybridization conditions. A strong hybridization signal corresponding to the 2 kb ECA1 transcript is identified in two of four endometrioid carcinomas of the ovary (E) (top panel). No expression was detected in serous carcinomas (SC), Brenner's ovarian tumor (B), clear cell carcinoma of the ovary (CC), a sarcoma cell line (S) or normal ovary (O). Ethidium bromide-stained 28S and 18S ribosomal RNAs are also shown (bottom panel).

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook et al. MOLECULAR CLONING: A LABORATORY MANUAL, $2^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc.); PCR: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1988)); and ANIMAL CELL CULTURE (R. I. Freshney ed. (1987)).

DEFINITIONS

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

A neoplasm is an abnormal mass or colony of cells produced by a relatively autonomous new growth of tissue. Most neoplasms arise from the clonal expansion of a single cell that has undergone neoplastic transformation. The transformation of a normal to a neoplastic cell can be caused by a chemical, physical, or biological agent (or event) that directly and irreversibly alters the cell genome. Neoplastic cells are characterized by the loss of some specialized functions and the acquisition of new biological properties, foremost, the property of relatively autonomous (uncontrolled) growth. Neoplastic cells pass on their heritable biological characteristics to progeny cells.

The past, present, and future predicted biological behavior, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm has a lesser degree of autonomy, is usually not invasive, does not metastasize, and generally produces no great harm if treated adequately. Cancer is a generic term for malignant neoplasms. Anaplasia is a characteristic property of cancer cells and denotes a lack of normal structural and functional characteristics (undifferentiation).

A tumor is literally a swelling of any type, such as an inflammatory or other swelling, but modern usage generally denotes a neoplasm. The suffix "-oma" means tumor and usually denotes a benign neoplasm, as in fibroma, lipoma, and so forth, but sometimes implies a malignant neoplasm, as with so-called melanoma, hepatoma, and seminoma, or even a non-neoplastic lesion, such as a hematoma, granuloma, or hamartoma. The suffix "-blastoma" denotes a neoplasm of embryonic cells, such as neuroblastoma of the adrenal or retinoblastoma of the eye.

One system to classify neoplasia utilizes biological (clinical) behavior, whether benign or malignant, and the histogenesis, the tissue or cell of origin of the neoplasm as determined by histologic and cytologic examination. Neoplasms may originate in almost any tissue containing cells capable of mitotic division. The histogenetic classification of neoplasms is based upon the tissue (or cell) of origin as determined by histologic and cytologic examination. Adenomas are benign neoplasms of glandular epithelium. Carcinomas are malignant tumors of epithelium. Sarcomas are malignant tumors of mesenchymal tissues.

"Suppressing" tumor growth indicates a growth state that is curtailed compared to growth without therapeutic intervention. Tumor cell growth can be assessed by any means known in the art, including, but not limited to, measuring tumor size, determining whether tumor cells are proliferating using a $^{3}$H-thymidine incorporation assay, or counting tumor cells. "Suppressing" tumor cell growth means any or all of the following states: slowing, delaying, and "suppressing" tumor growth indicates a growth state that is curtailed when stopping tumor growth, as well as tumor shrinkage.

A "native" or "natural" or "wild-type" antigen is a polypeptide, protein or a fragment which contains an epitope, which has been isolated from a natural biological source, and which can specifically bind to an antigen receptor, in particular a T cell antigen receptor (TCR), in a subject.

The term "antigen" is well understood in the art and includes substances which are immunogenic, i.e., immunogens, as well as substances which induce immunological unresponsiveness, or anergy, i.e., anergens.

A "self-antigen" also referred to herein as a native or wild-type antigen is an antigenic peptide that induces little or no immune response in the subject due to self-tolerance to the antigen. An example of a self-antigen is the melanoma specific antigen gp100.

The term "tumor associated antigen" or "TAA" refers to an antigen that is associated with or specific to a tumor. Examples of known TAAs include gp100, MART and MAGE.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

As used herein an "active fragment" of a gene or polypeptide includes smaller portion(s) (subsequences) of the gene or nucleic acid derived therefrom (e.g., cDNA) that retain the ability to encode proteins having tumor suppressing activity. Similarly, an active fragment of a polypeptide refers to a subsequence of a polypeptide that has tumor suppressing protein.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W. H. Freeman and Company. In addition, individual substitutions, deletions or additions which alter, add or delete a single amino acid or a small percentage of amino acids in an encoded sequence are also "conservatively modified variations".

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. (1989) supra). Similarly, an eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

The term "contacting a cell" when referring to contacting with an agent and/or polynucleotide is used herein to refer to contacting in a manner such that the agent and/or polynucleotide is internalized into the cell. In this context, contacting a cell with a nucleic is equivalent to transfecting a cell with a nucleic acid. Where the agent is lipophilic or the nucleic acid is complexed with a lipid (e.g., a cationic lipid) simple contacting will result in transport (active, passive and/or diffusive) into the cell. Alternatively the agent and/or polynucleotide, or in combination with a carrier composition be actively transported into the cell. Thus, for example, where the nucleic acid is present in an infective vector (e.g., an adenovirus) the vector may mediate uptake of the nucleic acid into the cell. The polynucleotide may be complexed to agents which interact specifically with extracellular receptors to facilitate delivery of the nucleic acid into the cell, examples include ligand/polycation/DNA complexes as described in U.S. Pat. Nos. 5,166,320 and 5,635,383. Additionally, viral delivery may be enhanced by recombinant modification of the knob or fiber domains of the viral genome to incorporate cell targeting moieties.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Zaks et al. (1999) Nat. Med. 7:823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad), pseudo adenoviral or adeno-associated virus (AAV), vector construct refers to the polynucleotide comprising the viral genome or part thereof, and a transgene. Adenoviruses (Ads) are a relatively well characterized, homogenous group of viruses, including over 50 serotypes. See, e.g., WO 95/27071. Ads are easy to grow and do not require integration into the host cell genome. Recombinant Ad-derived vectors, particularly those that reduce the potential for recombination and generation of wild-type virus, have also been constructed. See, WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, nucleic acids or proteins of this invention can be conjugated to antibodies or binding fragments thereof which bind cell surface antigens, e.g., TCR, CD3 or CD4.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6× SSC to about 10× SSC; formamide concentrations of about 0% to about 25%; and wash solutions of about 6× SSC. Examples of moderate hybridization conditions include: incubation temperatures of about 40° C. to about 50° C.; buffer concentrations of about 9× SSC to about 2× SSC; formamide concentrations of about 30% to about 50%; and wash solutions of about 5× SSC to about 2× SSC. Examples of high stringency conditions include: incubation temperatures of about 55° C. to about 68° C.; buffer concentrations of about 1× SSC to about 0.1× SSC; formamide concentrations of about 55% to about 75%; and wash solutions of about 1× SSC, 0.1× SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. One alignment program is BLAST, using default parameters. Alternative programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the website maintained by the Nation Center for Biotechnology Information at the National [Libray of Medicne] *Library of Medicine* using the Basic Local Alignment Search Tool (BLAST). Comparable programs are available for determining amino acid sequence identity.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

"Host cell," "target cell" or "recipient cell" are intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, simian or human.

A "subject" is a vertebrate, preferably a mammal, more preferably a human. Mammals include, but are not limited to, murines, simians, humans, farm animals, sport animals, and pets.

A "control" is an alternative subject or sample used in an experiment for comparison purpose. A control can be "positive" or "negative". For example, where the purpose of the experiment is to determine a correlation of an altered expression level of a gene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.). Solid supports also include microchips and grids, on which cDNAs, polynucleotides, peptides, antibodies or other molecules are fixed in arrays. The surface of the grids may be composed of a wide variety of material including glass, plastic, silicon, gold, gelatin or nylon. For example, the use of the so-called SELDI-MS method (surface-enhanced laser desorption-ionization & mass spectroscopy) exposes samples to chips with biochemically characterized surfaces (containing molecules such as antibodies or receptors) followed by mass spectroscopy to visualize and identify the bound proteins. For a review of recently available technology see Srivinas, P. et al. (2001) Clin. Chem. 47(10):1901-1911, and references cited therein such as De Wildt, R. M. T. et al. (2000) Nat. Biotech 18:989-94, Arenkov, P. et al. (2000) Anal. Biochem. 278:123-31, Haab, B. B. et al. (2001) Genome Biol. 2:1-13, and Cahill, D. J. (2001) J Immunol. Methods 250:81-91. Also included within a solid support are tissue microarrays in which small cylinders of tissue are punched out of thousands of individual tumor specimens (from different tissues of hundreds of individuals in a study) and then probed with antibodies, RNA, etc. Hoos, A. et al. (2001) Am. J. Pathol. 158:1245-51.

The term "immunomodulatory agent", as used herein, is a molecule, a macromolecular complex, or a cell that modulates an immune response and encompasses an antigenic peptide of the invention alone or in any of a variety of formulations described herein; a polypeptide comprising an antigenic peptide of the invention; a polynucleotide encoding a peptide or polypeptide of the invention; an antigenic peptide of the invention bound to a Class I or a Class II MHC molecule on an antigen-presenting matrix, including an APC and a synthetic antigen-presenting matrix (in the presence or absence of co-stimulatory molecule(s)); an antigenic peptide of the invention covalently or non-covalently complexed to another molecule(s) or macromolecular structure; and an educated, antigen-specific immune effector cell which is specific for a peptide of the invention.

The term "modulate an immune response" includes inducing (increasing, eliciting) an immune response; and reducing (suppressing) an immune response. An immunomodulatory method (or protocol) is one that modulates an immune response in a subject.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1α), interleukin-11 (IL-11), MIP-11, leukemia inhibitory factor (LIF), c-kit ligand, [thrombopoictin] *thrombopoietin* (TPO) and flt3 ligand. The present invention also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

A "composition" is intended to mean a combination of active agent and another compound or composition, inert (for example, a detectable agent or label or a solid support) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages.

ECA1 Polynucleotides

This invention provides polynucleotide sequences that encode ECA1 polypeptides. Polynucleotides include, for example, genomic DNA, mRNA, antisense RNA, cDNA and modifications thereof. In one aspect the polynucleotides sequences are modified in a variety of ways, such as mixed backbone polynucleotides which comprise both deoxy and ribo nucleotides. Also provided are polynucleotides that are truncated fragments of these polynucleotides, e.g., genomic DNA, mRNA, antisense RNA, cDNA and modifications thereof.

Also intended to be included are the functional equivalents of ECA1 polynucleotides. In one aspect, functional equivalents are identified by hybridization to a polynucleotide that encodes SEQ ID NO.:1 under moderate and/or stringent conditions. Alternatively, functional equivalents are identified by having more that 80%, or alternatively, more that 85%, or alternatively, more than 90%, or alternatively, more than 95%, or alternatively more than 97%, or alternatively, more than 98 or 99% sequence homology to a sequence that encodes SEQ ID NO.: 1 (e.g., SEQ ID NO.: 2) as determined by sequence comparison programs such as BLAST run under appropriate conditions. In one aspect, the program is run under default parameters.

In one aspect, the polynucleotides are detectably labeled by known techniques. Examples of labels include, but are not limited to radioactive labels, fluorescent labels and enzymes.

Polynucleotides of this invention can be prepared by the art recognized methods such as phosphoramidite or H-phosphonate chemistry which can be carried out manually or by an automated synthesizer as described in Uhlmann et al. (Chem. Rev. (1990) 90:534-583). The polynucleotides may be composed of ribonucleotides, deoxyribonucleotides, or a combination of both.

Alternatively, the polynucleotides can be replicated using PCR or gene cloning techniques. Thus, this invention also provides a polynucleotide of this invention operatively linked to elements necessary for the transcription and/or translation of these polynucleotides in host cells. In one aspect, the polynucleotide is a component of a gene delivery vehicle for insertion into the host cells. Host cells include eukaryotic and prokaryotic cells, such as bacterial cells, yeast cells, simian cells, murine cells and human cells. The cells can be cultured or recently isolated from a subject. The host cells are cultured under conditions necessary for the recombinant production of the polypeptide or recombinant replication of the polynucleotides. Recombinantly produced polynucleotides and/or polynucleotides are further provided herein.

In one embodiment the polynucleotides of the invention are modified to be composed of ribonucleotides and deoxyribonucleotides with the 5' end of one nucleotide and the 3' end of another nucleotide being covalently linked to produce mixed backbone polynucleotides (e.g., U.S Pat. Nos.: 5,652,355; 5,264,423; 5,652,356; and 5,591,721). The mixed backbone polynucleotides may be of varying length preferably being at least about 14 nucleotides in length, most preferably 15 to 28 nucleotides long, with 15- to 25-mers being the most common. The mixed backbone polynucleotide may be any combination of ribonucleotides and deoxyribonucleotides. By way of example, the mixed backbone polynucleotide may comprise a [contigous] *contiguous* stretch of deoxynucleotides (e.g., about 14 to about 8) flanked on either side by ribonucleotides (e.g., about 2 to about 4). The phosphodiester bond may be replaced with any number of chemical groups such as, for example, phosphothioate.

Antisense nucleic acid sequences of the invention can impair the activity of the ECA1 gene in a variety of ways and via interaction with a number of cellular products. Examples include, but are not limited to, the hydrolysis action catalyzed by [RNAse] *RNase* H, the formation of triple helix structures with the duplex DNA encoding ECA1, interaction with the intron-exon junctions of pre-messenger RNA, hybridization with messenger RNA in the cytoplasm resulting in an RNA-DNA complex which is degraded by the [RNAase] *RNase* H enzyme, or by blocking the formation of the ribosome-mRNA complex and thus blocking the translation of ECA1.

In one aspect, the polynucleotides are modified in that they contain a detectable label, for example, a radionucleotide or an enzymatic label. Labels are commercially available. Methods for conjugating a label to a polynucleotide are known in the art.

ECA1 Polypeptides

This invention also provides isolated ECA1 polypeptides. In one aspect, the polypeptide has the amino acid sequence shown in SEQ ID NO.:1. In another aspect, the polypeptide is modified by substitution with conservative amino acids. In yet a further aspect, the polypeptide has the same function as the polypeptide of SEQ ID NO: 1 as determined using the examples set forth below and are identified by having more than 80%, or alternatively, more than 85%, or alternatively, more than 90%, or alternatively, more than 95%, or alternatively more than 97%, or alternatively, more than 98 or 99% sequence homology to SEQ ID NO.: 1 as determined by sequence comparison programs such as BLAST run under appropriate conditions. In one aspect, the program is run under default parameters. Further provided are active fragments of these embodiments.

The peptides used in accordance with the method of the present invention can be obtained in any one of a number of conventional ways. For example, they can be prepared by chemical synthesis using standard techniques. Particularly convenient are the solid phase peptide synthesis techniques. Automated peptide synthesizers are commercially available, as are the reagents required for their use.

In one embodiment, isolated peptides of the present invention can be synthesized using an appropriate solid state synthetic procedure. Steward and Young, eds. (1968) SOLID PHASE PEPTIDE SYNTHESIS, Freemantle, San Francisco, Calif. One method is the Merrifield process. Merrifield (1967) Recent progress in Hormone Res. 23:451. Once an isolated peptide of the invention is obtained, it may be purified by standard methods including chromatography (e.g., ion exchange, affinity, and sizing column chromatography), centrifugation, differential solubility, or by any other standard technique for protein purification. For immunoaffinity chromatography, an epitope may be isolated by binding it to an affinity column comprising antibodies that were raised against that peptide, or a related peptide of the invention, and were affixed to a stationary support.

Alternatively, affinity tags such as hexa-His (Invitrogen), Maltose binding domain (New England Biolabs), influenza coat sequence (Kolodziej et al. (1991) Methods Enzymol. 194:508-509), and glutathione-S-transferase can be attached to the peptides of the invention to allow easy purification by passage over an appropriate affinity column. Isolated peptides can also be physically characterized using such techniques as proteolysis, nuclear magnetic resonance, and x-ray crystallography.

Alternatively, the polynucleotides can be replicated using PCR or gene cloning techniques. Thus, this invention also provides a polynucleotide of this invention operatively linked to elements necessary for the transcription and/or translation of these polynucleotides in host cells. In one aspect, the polynucleotide is a component of a gene delivery vehicle for insertion into the host cells. The means by which the cells may be transformed with the expression construct includes, but is not limited to, microinjection, electroporation, transduction, transfection, lipofection, calcium phosphate particle bombardment mediated gene transfer or direct injection of nucleic acid sequences or other procedures known to one skilled in the art (Sambrook et al. (1989) supra). For various techniques for transforming mammalian cells, see, e.g., Keown et al. (1990) Methods in Enzymology 185:527-537).

Host cells include eukaryotic and prokaryotic cells, such as bacterial cells, yeast cells, simian cells, murine cells and human cells. The cells can be cultured or recently isolated from a subject. The host cells are cultured under conditions necessary for the recombinant production of the polypeptide or recombinant replication of the polynucleotides. Recombinantly produced polynucleotides and/or polynucleotides are further provided herein.

Also included within the scope of the invention are polypeptides that are differentially modified during or after translation, e.g., by phosphorylation, glycosylation, crosslinking, acetylation, proteolytic cleavage, linkage to an antibody molecule, membrane molecule or other ligand. Ferguson et al. (1988) Ann. Rev. Biochem. 57:285-320. This is achieved using various chemical methods or by expressing the polynucleotides in different host cells, e.g., bacterial, mammalian, yeast, or insect cells.

Also provided by this invention are peptide fragments, e.g., [immunogeneic] *immunogenic* or antigenic portions, alone or in combination with a carrier. An antigenic peptide epitope of the invention can be used in a variety of formulations, which may vary depending on the intended use.

An antigenic peptide epitope of the invention can be covalently or non-covalently linked (complexed) to various other molecules, the nature of which may vary depending on the particular purpose. For example, a peptide of the invention can be covalently or non-covalently complexed to a macromolecular carrier, including, but not limited to, natural and synthetic polymers, proteins, polysaccharides, poly(amino acid), polyvinyl alcohol, polyvinyl pyrrolidone, and lipids. A peptide can be conjugated to a fatty acid, for introduction into a liposome. U.S. Pat. No. 5,837,249. A synthetic peptide of the invention can be complexed covalently or non-covalently with a solid support, a variety of which are known in the art. An antigenic peptide epitope of the invention can be associated with an antigen-presenting matrix with or without co-stimulatory molecules, as described in more detail below.

Examples of protein carriers include, but are not limited to, superantigens, serum albumin, tetanus toxoid, ovalbumin, thyroglobulin, myoglobulin, and immunoglobulin.

Peptide-protein carrier polymers may be formed using conventional crosslinking agents such as carbodiimides. Examples of carbodiimides are 1-cyclohexyl-3-(2-morpholinyl-(4-ethyl) carbodiimide (CMC), 1-ethyl-3-(3-dimethyaminopropyl) carbodiimide (EDC) and 1-ethyl-3-(4-azonia-44-dimethylpentyl) carbodiimide.

Examples of other suitable crosslinking agents are cyanogen bromide, glutaraldehyde and succinic anhydride. In general, any of a number of homobifunctional agents including a homobifunctional aldehyde, a homobifunctional epoxide, a homobifunctional imidoester, a homobifunctional N-hydroxysuccinimide ester, a homobifunctional maleimide, a homobifunctional alkyl halide, a homobifunctional pyridyl disulfide, a homobifunctional aryl halide, a homobifunctional hydrazide, a homobifunctional diazonium derivative and a homobifunctional photoreactive compound may be used. Also included are heterobifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homobifunctional crosslinking agents include the bifunctional N-hydroxysuccinimide esters dithiobis(succinimidylpropionate), disuccinimidyl suberate, and disuccinimidyl tartarate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio) propion-amido]butane, bis-maleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl] disulfide; the bifunctional aldehydes formaldehyde, malondialdehyde, succinaldehyde, glutaraldehyde, and adipaldehyde; a bifunctional epoxide such as 1,4-butaneodiol diglycidyl ether, the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis(iodoacetarnide), N1N'-hexamethylene-bis(iodoacetamide), N1N'-undecamethylene-bis(iodoacetamide), as well as benzylhalides and halomustards, such as a1a'-diiodo-p-xylene sulfonic acid and tri(2-chloroethyl)amine, respectively.

Examples of other common heterobifunctional cross-linking agents that may be used to effect the conjugation of proteins to peptides include, but are not limited to, SMCC succinimidyl-4-(N-maleimidomethyl)cyclohexane-1-carboxylate), MBS (m-maleimidobenzoyl-N-hydroxysuccinimide ester), SLAB (N-succinimidyl(4-iodoacteyl)aminobenzoate), SMPB (succinimidyl-4-(p-maleimidophenyl) butyrate), GMBS (N-(γ-maleimidobutyryloxy)succinimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-á-methyl-á-(2-pyridyldithio)toluene), and SPDP (N-succinimidyl 3-(2-pyridyldithio)propionate).

Crosslinking may be accomplished by coupling a carbonyl group to an amine group or to a hydrazide group by reductive amination.

Peptides of the invention also may be formulated as non-covalent attachment of monomers through ionic, adsorptive, or biospecific interactions. Complexes of peptides with highly positively or negatively charged molecules may be done through salt bridge formation under low ionic strength environments, such as in deionized water. Large complexes can be created using charged polymers such as poly-(L-glutamic acid) or poly-(L-lysine) which contain numerous negative and positive charges, respectively. Adsorption of peptides may be done to surfaces such as microparticle latex beads or to other hydrophobic polymers, forming non-covalently associated peptide-superantigen complexes effectively mimicking crosslinked or chemically polymerized protein. Finally, peptides may be non-covalently linked through the use of biospecific interactions between other molecules. For instance, utilization of the strong affinity of biotin for proteins such as avidin or streptavidin or their derivatives could be used to form peptide complexes. These biotin-binding proteins contain four binding sites that can interact with biotin in solution or be covalently attached to another molecule. Wilchek (1988) Anal Biochem. 171:1-32. Peptides can be modified to possess biotin groups using common biotinylation reagents such as the N-hydroxysuccinimidyl ester of D-biotin (NHS-biotin) which reacts with available amine groups on the protein. Biotinylated peptides then can be incubated with avidin or streptavidin to create large complexes. The molecular mass of such polymers can be regulated through careful control of the molar ratio of biotinylated peptide to avidin or streptavidin.

Also provided by this application are the peptides and polypeptides described herein conjugated to a detectable agent for use in the diagnostic methods. For example, detectably labeled peptides and polypeptides can be bound to a column and used for the detection and purification of antibodies. They also are useful as immunogens for the production of antibodies, as described below.

The peptides of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to non-specifically augment a specific immune response. A skilled artisan can easily determine whether an adjuvant is required and select one. However, for the purpose of illustration only, suitable adjuvants include, but are not limited to, Freund's Complete and Incomplete, mineral salts and polynucleotides.

Expression Levels of ECA1

The level of ECA1 expression may be measured by conventional methodology. By way of example, the level of expression of ECA1 RNA may be measured by Northern Blot Analysis, Polymerase Chain Analysis and the like (See e.g. Sambrook et al. (eds.) (1989) supra; Ausubel et al. (eds.) (1987) "Current Protocols in Molecular Biology" John Wiley and Sons, New York, N.Y.). Likewise the level of ECA1 protein may be measured by conventional methodology, including, but not limited to, Western Blot Analysis or ELISA (see e.g. Sambrook et al. (eds.) (1989) supra and Ausubel et al. (eds.) (1987) supra).

ECA1 RNA levels, or ECA1 protein levels, or other indicia of ECA1 expression may also be measured at different times (i.e., sequentially) so as to monitor the progression of a disease, e.g., ovarian cancer in a subject. Such sequential measurements may also be used to monitor the disease status of a subject who is at risk for a disease, e.g., an ovarian cancer cell, a colon carcinoma, a small cell lung carcinoma and a metastatic chondrosarcoma cell. The status of a disease state in a subject may also be determined by reference to previous measurements made in a comparable subject.

Screening Assay

A screening assay for assessing the therapeutic potential of a candidate agent, such as ECA1 antisense polynucleotides, may be performed using cells exhibiting overexpression of ECA1. A variety of parameters may be used to assess the therapeutic potential of a candidate agent, as described herein.

The method of assessing the therapeutic potential of an agent to inhibit cancer cell proliferation may comprise: (i) contacting cells exhibiting overexpression of ECA1 growth activity with at least one candidate, and (ii) measuring the level of ECA1 expression or activity or cell growth, wherein an inhibition in ECA1 expression or cell growth is indicative of the candidate agent's therapeutic potential. The term inhibition includes a reduction, decrease, [dimunition] *diminution* or abolition of ECA1 expression, activity or cellular proliferation. An inhibition in either ECA1 expression or cell growth also provides information relevant to determining the dosage range of the agent that may be used in vivo therapy. To determine if the level of ECA1 is altered by the candidate agent, comparison may be made to cells not exposed to the candidate agent or any other suitable control. A suitable cells that constitutively overexpress ECA1 include, for example, an ovarian cancer cell, a colon carcinoma, a small cell lung carcinoma and a metastatic chondrosarcoma cell.

Any cell overexpressing ECA1 may be used in the screening assay. Preferably the cell lines are mammalian cancer cells, most preferably human cancer cells. Non-limiting examples of cancer cell lines that may be used include, but are not limited to, cells of endometrioid origin, e.g., ovarian cancer cells, colon carcinoma, cells, small cell lung carcinoma cells, and metastatic chondrosarcoma cells. Alternatively, the cells used in the methods may be primary cultures (e.g., developed from biopsy or necropsy specimens) or cells engineered to overexpress ECA1 in culture. Methods of maintaining primary cell cultures or cultured cell lines are well known to those of skill in the art.

To enhance the sensitivity of the screening assay, the cells may be transformed with a construct comprising nucleic acid sequences encoding ECA1 to produce cells expressing a higher level of ECA1. The nucleic acid sequences encoding ECA1 may be cDNA or genomic DNA or a fragment thereof, preferably the coding sequence used is sufficient to effect ECA1 expression. Vectors suitable for use in expressing the ECA1 gene are constructed using conventional methodology (See e.g. Sambrook et al. (eds.) (1989) supra and Ausubel et al. (eds.) (1987) supra) or are commercially available.

The means by which the cells may be transformed with the expression construct includes, but is not limited to, microinjection, electroporation, transduction, transfection, lipofection calcium phosphate particle bombardment mediated gene transfer or direct injection of nucleic acid sequences or other procedures known to one skilled in the art (Sambrook et al. (1989) supra). For various techniques for transforming mammalian cells, see, e.g., Keown et al. (1990) Methods in Enzymology 185:527-537). One of skill in the art will appreciate that vectors may not be necessary for the antisense polynucleotides applications of the subject invention. Antisense polynucleotides may be introduced into a cell, preferably a cancer cell, by a variety of methods, including, but not limited to, liposomes or lipofection (Thierry, A. R. et al (1993) Biochem Biophys Res Commun 190:952-960; Steward, A. J. et al (1996) Biochem Pharm 51:461-469) and calcium phosphate.

Other Candidate Agents

Other candidate agents suitable for assaying according to the methods of the subject application may be any type of molecule from, for example, chemical, nutritional or biological sources. The candidate agent may be a naturally occurring or synthetically produced. For example, the candidate agent may encompass numerous chemical classes, though typically they are organic molecule, preferably small organic compounds having a molecular weight of more than 50 and less than about 2,500 Daltons. Such molecules may comprise functional groups necessary for structural interaction with proteins or nucleic acids. By way of example, chemical agents may be novel, untested chemicals, agonists, antagonists, or modifications of known therapeutic agents.

The agents may also be found among biomolecules including, but not limited to, peptides, saccharides, fatty acids, antibodies, steroids, purines, pryimidines, toxins conjugated cytokines, derivatives or structural analogs thereof or a molecule manufactured to mimic the effect of a biological response modifier. Examples of agents from nutritional sources include, but is not limited to, extracts from plant or animal sources or extracts thereof. Examples include antisense polynucleotides or antibodies.

The agents may be obtained from a wide variety of sources including libraries of synthetic or natural compounds. Alternatively, libraries of natural compounds in the form of bacterial, fungal, plant, and animal extracts are available or readily produced, natural or synthetically produced libraries or compounds are readily modified through conventional chemical, physical and biochemical means, and may be used to produce combinatorial libraries. Known pharmacological agents may be subjected to random or directed chemical modifications, such as acetylation, alkylation, esterification, amidification, etc. to produce structural analogs.

The candidate agents which are antagonists of ECA1 may inhibit abnormal cellular proliferation in a variety of ways. For example, the antagonist may be capable of inhibiting the production of ECA1, or interfere with the binding of ECA1 to its cognate receptors or interfere with the biological effects of ECA1. Examples include, but are not limited to, antibodies against ECA1 or its receptors, soluble forms of ECA1 that bind ECA1 away from the cells, or agents that inhibit transmission of ECA1 binding into the cell can also be used.

ECA1 is highly homologous to wingful/Notum protein of fruit fly; the recently identified secreted putative feedback inhibitor of Wingless. Phylogenetic analysis has revealed that Notum/wingful and ECA1 are [othologs] *orthologs* and perform similar function. Notum/wingful is reported to inhibit Wingless activity by enzymatically modifying the heparan sulfate proteoglycans (HSPGs). Similar to Notum/wingful, ECA1 harbors a signal peptide and belongs to $\alpha/\beta$ hydrolase family of enzymes. ECA1 harbors the $\alpha/\beta$ hydrolase consensus active site motif G-X-S-X-G (SEQ ID NO.: 7; G is glycine, X could be any amino acid and S is the nucleophile serine) also known as "nucleophile elbow". The conserved Ser 170 of the nucleophile elbow, in addition to Asp 278 and His 327 are predicted to form the catalytic active site. It is conceivable that ECA1 putative enzymatic activity may be inhibited using molecules that have structural similarity to ECA1 substrate that may or may not fit in the catalytic active site and act as competitive inhibitors, "mixed" agonist/antagonists or complete antagonists.

Identification, Analysis, and Manipulation of Genetic Polymorphisms With SNP Technology An isolated ECA1 polynucleotide can be used to search for and identify single nucleotide polymorphisms ([SNP's] *SNPs*), (see, e.g., the polymorphisms described in FIG. 2.) which are mutant variants of the gene in the human population. Identification of such polymorphisms is useful to define human diseases to which mutations in the genes contribute and to perfect therapies for disease processes in which the protein encoded by the genes participates. Mutant variants of the gene identified in this manner can then be employed in the development, screening, and analysis of pharmaceutical agents to treat these diseases. Methods to detect such [SNP's] *SNPs* can be formatted to create diagnostic tests. Furthermore, various mutations in the gene which effect the response of different individuals to therapeutic agents can be identified and then diagnosed through analysis of [SNP's] *SNPs*, to guide the prescription of appropriate treatments. Also, [SNP's] *SNPs* identified in the genes can provide useful sequence markers for genetic tests to analyze other genes and mutations in the region of the genome where the gene(s) is located. Thus it is useful to incorporate these [SNP's] *SNPs* into polymorphism databases.

Skilled practitioners of the art are familiar with an array of methods for identifying and analyzing [SNP's] *SNPs*. High throughput DNA sequencing procedures such as sequencing by hybridization (Drmanac et al. (1993) Science 260:1649-52), minisequencing primer extension (Syvanen, (1999) Hum. Mutat. 13(1):1-10), or other sequencing methods can be used to detect SNP's in defined regions of the gene. Alternatively, hybridization to oligonucleotides on DNA microarrays (Lipshutz et al. (1999) Nat. Genet. 21(1 Suppl.):20-4) analysis of single strand conformational polymorphisms in DNA or RNA molecules by various analytical methods (Nataraj (1999 Wiley & Sons, United Kingdom) pp: 277-297; Dorin et al. (1992) Nature 359:211-215) and Electrophoresis 20(6):1177-85), PCR-based mutational analyses such as PCR with primers spanning the polymorphic sequence, or protection of SNP-containing oligonucleotides from nuclease protection such as by use of the bacterial mutS protein can be employed. Many sophisticated high-throughput technologies based on methods such as automated capillary electrophoresis (Larsen et al. (1999) Hum. Mutat. 13(4):318-27), time-of-flight mass spectroscopy, high density micro-arrays (Sapolsky et al. (1999) Genet. Anal. 14(5-6):187-92), semiconductor microchips (Gilles et al. (1999) Nature Biotechnol. 17(4):365-70), and others have been demonstrated that can be employed with the gene(s) to perform the uses described above.

Immunotherapeutic Compositions and Methods

The present invention also provides polyclonal and/or monoclonal antibodies, including fragments and immunologic binding equivalents thereof, which are capable of specifically binding to the polynucleotide sequences of the specified gene and fragments thereof, as well as the corresponding gene products and fragments thereof. The therapeutic potential of the antibodies may be evaluated in the screening methods described herein. In general, techniques for preparing polyclonal and monoclonal antibodies as well as hybridomas capable of producing the desired antibody are well known in the art. These include, e.g., the trioma technique and the human B-cell hybridoma technique.

Antibodies may be generated using standard techniques described herein or using conventional techniques, such as described in U.S. Pat. Nos. 5,837,492; 5,800,998 and 5,891,628, against the proteins themselves or against peptides corresponding to the binding domains of the proteins. Such antibodies include but are not limited to polyclonal, monoclonal, Fab fragments, F(ab').sub.2 fragments, single chain antibodies, chimeric antibodies, humanized antibodies etc.

Any animal (mouse, rabbit, etc.) that is known to produce antibodies can be immunized with the immunogenic composition. Methods for immunization are well known in the art and include subcutaneous or intraperitoneal injection of the immunogen. One skilled in the art will recognize that the amount of the protein encoded by the nucleic acids of the present invention used for immunization will vary based on the animal which is immunized, the antigenicity of the immunogen, and the site of injection. The protein which is used as an immunogen may be modified or administered in an adjuvant to increase its antigenicity. Methods of increasing antigenicity are well known in the art and include, but are not limited to, coupling the antigen with a heterologous protein (such as globulin, β-galactosidase, KLH, etc.) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify hybridoma cells that produce an antibody with the desired characteristics. These include screening the hybridomas with an enzyme-linked immunosorbent assay (ELISA), western blot analysis, or radioimmunoassay (RIA). Hybridomas secreting the desired antibodies are cloned and the immunoglobulin class and subclass may be determined using procedures known in the art. Hybridoma cell lines are also provided by this invention.

Techniques described for the production of single chain antibodies (U.S. Pat. No. 4,946,778) can be adapted to produce single chain antibodies to the proteins of the present invention. For polyclonal antibodies, antibody-containing antisera is isolated from an immunized animal and is screened for the presence of antibodies with the desired specificity using one of the above described procedures.

Antibodies may be used in a labeled form to permit detection. Antibodies can be labeled, e.g., through the use of radioisotopes, affinity labels (such as biotin, avidin, etc.), enzymatic labels (such as horseradish peroxidase, alkaline phosphatase, etc.) fluorescent labels (such as fluorescein or rhodamine, etc.), paramagnetic atoms, etc. Procedures for accomplishing such labeling are known in the art. The labeled antibodies of the present invention can then be used for in vitro, in vivo, and in situ assays to identify the cells or tissues in which a fragment of the polypeptide of interest is expressed. Examples of immunoassays are the various types of ELISAs and RIAs known in the art. The antibodies themselves also may be used directly in therapies or as diagnostic reagents.

Compositions containing the antibodies, fragments thereof or cell lines which produce the antibodies, are encompassed by this invention. When these compositions are to be used pharmaceutically, they are combined with a pharmaceutically acceptable carrier.

The methods of the invention are useful to detect and isolate specific antigenic polypeptides, antibody-reactive peptide epitopes and therapeutic antibody molecules. These compositions have a variety of uses for diagnosing and inhibiting pathological cells. For example, antigen-reactive antibodies can be generated by immunizing an animal with the antigenic polypeptide using methods well known in the art. It is also desirable to prepare a monoclonal antibody for administration to a subject. For use with human subjects, methods have now been established to produce "humanized antibodies" where species specific portions of the antibody molecule have been converted to sequences characteristic of human antibodies. Such molecules function more effectively when administered to a human subject.

Diagnostic antibodies are useful for detecting a pathological cell and a variety of alternative techniques for labeling and detecting these antibodies have been established. For example, the antibody can be conjugated to a radioactive isotope that can be localized in the subject following administration of the antibody.

Therapeutic antibodies can also be administered to a subject to inhibit the progression of disease. In a human subject it is desirable to administer a humanized monoclonal antibody for this purpose. The antibody can confer a passive immunity wherein it inhibits disease by binding to antigens in the target pathological tissue and inducing complement mediated cytotoxicity, antibody-directed cytotoxicity, or interference with receptor-ligand interactions. Alternatively, administration of an antibody to a subject can vaccinate against disease by inducing an anti-idiotype immune response. For use in a human subject a monoclonal antibody such as a mouse monoclonal antibody is effective for this purpose.

The antigenic polypeptides identified by practicing the methods of the invention are also useful as therapeutic agents when administered to a subject or useful to educate naïve immune effector cells. Such polypeptides can be formulated with an adjuvant and administered as a vaccine to induce an immune response against the pathological target tissue. Such antigenic polypeptides can also be administered ex vivo, for example to dendritic cells isolated from the subject. The antigen pulsed dendritic cells can then be expanded in culture and returned to the subject to perform adoptive immunotherapy.

In another embodiment the present invention provides a method of inducing an immune response comprising delivering the compounds and compositions of the invention in the context of an MHC molecule. Thus, the polypeptides of this invention can be pulsed into antigen presenting cells using the methods described herein. Antigen-presenting cells, include, but are not limited to dendritic cells (DCs), monocytes/macrophages, B lymphocytes or other cell type(s) expressing the necessary MHC/co-stimulatory molecules. The methods described below focus primarily on DCs which are the most potent, preferred APCs. These host cells containing the polypeptides or proteins are further provided.

Isolated host cells which present the polypeptides of this invention in the context of MHC molecules are further useful to expand and isolate a population of educated, antigen-specific immune effector cells. The immune effector cells, e.g., cytotoxic T lymphocytes, are produced by culturing naïve immune effector cells with antigen-presenting cells which present the polypeptides in the context of MHC molecules on the surface of the APCs. The population can be purified using methods known in the art, e.g., FACS analysis or [ficoll]

*Ficoll* gradient. The methods to generate and culture the immune effector cells as well as the populations produced thereby also are the inventor's contribution and invention. Pharmaceutical compositions comprising the cells and pharmaceutically acceptable carriers are useful in adoptive immunotherapy. Prior to administration in vivo, the immune effector cells are screened in vitro for their ability to lyse cells expressing ECA1 epitope.

In one embodiment, the immune effector cells and/or the APCs are genetically modified. Using standard gene transfer, genes coding for co-stimulatory molecules and/or stimulatory cytokines can be inserted prior to, concurrent to or subsequent to expansion of the immune effector cells.

This invention also provides methods of inducing an immune response in a subject, comprising administering to the subject an effective amount of a polypeptide described above under the conditions that induce an immune response to the polypeptide. The polypeptide can be administered in a formulation or as a polynucleotide encoding the polypeptide. The polynucleotide can be administered in a gene delivery vehicle or by inserting into a host cell which in turn recombinantly transcribes, translates and processed the encoded polypeptide. Isolated host cells containing the polynucleotides of this invention in a pharmaceutically acceptable carrier can therefore be combined with appropriate and effective amount of an adjuvant, cytokine or co-stimulatory molecule for an effective vaccine regimen. In one embodiment, the host cell is an APC such as a dendritic cell. The host cell can be further modified by inserting of a polynucleotide coding for an effective amount of either or both a cytokine and/or a co-stimulatory molecule.

The methods of this invention can be further modified by co-administering an effective amount of a cytokine or co-stimulatory molecule to the subject.

Animal Model System

The anti-ECA1 agents may be evaluated first in animal models. The safety of the compositions and methods of treatment is determined by looking for the effect of treatment on the general health of the treated animal (weight change, fever, appetite behavior etc.) monitoring of generalized toxicity, electrolyte renal and hepatic function, hematological parameters and functional measurements. Pathological changes may be detected on autopsies.

Any animal based (e.g., recombinant and non-recombinant) model systems may be used to assess the in vivo efficacy of the ECA1 therapeutic agents, e.g., antisense polynucleotides or anti-ECA1 antibodies, and to provide effective dosage ranges. For example, the relevance of the cell culture findings to the ability of an anti-ECA1 monoclonal antibody to be used for the treatment of ovarian cancer can be confirmed by performing experiments in vivo in a mouse model.

Diseases

The therapeutic agents such as antisense polynucleotide or monoclonal antibodies, or the equivalents thereof, may be used to inhibit abnormal cellular proliferation. The agents have numerous therapeutic applications in a variety of diseases including, but not limited to, neoplastic conditions derived from the abnormal proliferation of cells of endometrioid origin, eg. ovarian cancer.

Administration of the antisense polynucleotides, or antibodies, serve to ameliorate, attenuate or abolish the abnormal proliferation of cells in the subject. Thus, for example, in a subject afflicted with cancer, the therapeutic administration of one or more of the antisense polynucleotides serves to attenuate or alleviate the cancer or facilitate regression of cancer in the subject. Also contemplated is administration of the antisense polynucleotides to a subject prior to any clinical signs of disease. Examples of such individuals includes, but is not limited to, subjects with a family history of ovarian cancer.

Effective Amounts

An effective or therapeutically effective amount of the therapeutic agents of the invention to be administered to a subject, or functional equivalents of the antagonists, may be determined in a variety of ways. By way of example, the antisense polynucleotides to be administered may be chosen based on their effectiveness in inhibiting the growth of cultured cancer cells that overexpress ECA1. Examples of such cell lines include, but are not necessarily limited to, ovarian cancer cells.

Effective concentrations of antisense polynucleotides can be determined by a variety of techniques other than inhibition of cultured cells. For example, another suitable assay that can be used is the determination of the effect of the antisense polynucleotide on mRNA levels in a cell. In one embodiment, antisense polynucleotides are capable of reducing mRNA levels for ECA1 by a factor of about 1.5 or more. In another embodiment, the antisense polynucleotide is capable of reducing the mRNA levels of 2 or more forms of ECA1 by a factor of about 2 or more.

Therapeutic agents may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods. The dosage may be modified in accordance with other treatments the individual may be receiving. However, the method of treatment is in no way limited to a particular concentration or range of the antisense polynucleotides or antibodies or functional equivalents thereof and may be varied for each individual being treated and for each derivative used.

For therapeutic purposes, one of skill in the art will appreciate that individualization of dosage may be required to achieve the maximum effect for a given individual. One skilled in the art will know the clinical parameters to evaluate to determine proper dosage for the individual being treated by the methods described herein. It is further understood by one skilled in the art that the dosage administered to a individual being treated may vary depending on the individuals age, severity or stage of the disease and response to the course of treatment. The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual polynucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues.

Following successful treatment, it may be desirable to have the patient undergo maintenance therapy to prevent the recurrence of the disease state, wherein the therapeutic agent is administered in maintenance doses, ranging from 0.01 μg to 100 g per kg of body weight, once or more daily, to once every 20 years. Clinical parameters that may be assessed for determining dosage include, but are not limited to, tumor size, alteration in the level of tumor markers used in clinical testing for particular malignancies. Based on such parameters the treating physician will determine the therapeutically effective amount to be used for a given individual. Such therapies may be administered as often as necessary and for the period of time judged necessary by the treating physician.

While it is possible for a therapeutic agent of the invention (or functional equivalents thereof) to be administered in a pure or substantially pure form, it is preferable to present it as a pharmaceutical composition, formulation or preparation.

Pharmaceutical Compositions

The present invention also includes pharmaceutical compositions and formulations which include the polynucleotide, polypeptide, antibody, APC or immune effector cell of the invention. The pharmaceutical compositions of the present invention may be administered in a number of ways, described herein, depending upon whether local or systemic treatment is desired and upon the area to be treated.

The formulations of the present invention, for both veterinary and human use, comprise one or more of the therapeutic agents together with one or more pharmaceutically acceptable carriers and, optionally, other active agents or therapeutic ingredients. The carrier(s) must be "acceptable" in the sense of being compatible with the other ingredients of the formulation and not deleterious to the recipient thereof. The characteristics of the carrier will depend on the route of administration. Such a composition may contain, in addition to the one or more polynucleotides and carrier, diluents, fillers, salts, buffers, stabilizers, solubilizers, and other materials well known in the art. The formulations may be prepared by any method well-known in the pharmaceutical art.

The therapeutic agents of the present invention can be formulated for parenteral administration, e.g., for injection via the intravenous, intramuscular, sub-cutaneous, intratumoral or intraperitoneal routes. The preparation of an aqueous composition that contains a therapeutic agent alone or in combination with another agent as active ingredients will be known to those of skill in the art in light of the present disclosure. Typically, such compositions can be prepared as injectables, such as liquid solutions or suspensions. Solid forms, that can be formulated into solutions or suspensions upon the addition of a liquid prior to injection, as well as emulsions, can also be prepared.

When oral preparations are desired, the component may be combined with typical carriers, such as lactose, sucrose, starch, talc magnesium stearate, crystalline cellulose, methyl cellulose, carboxymethyl cellulose, glycerin, sodium alginate or gum arabic among others.

In certain cases, the formulations of the invention could also be prepared in forms suitable for topical administration, such as in creams and lotions. These forms may be used for treating skin-associated diseases.

Additional pharmaceutical methods may be employed to control the duration of action. Controlled release preparations may be achieved through the use of polymer to complex or absorb the proteins or their derivatives. The controlled delivery may be exercised by, for example, selecting appropriate macromolecules known in the art, incorporating the one or more therapeutic agents either alone or in combination with other active agents into particles of a polymeric material (e.g., polyesters, polyamino acids etc) or entrapping these materials in microcapsules prepared, for example, by coacervation techniques or by interfacial polymerization.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Addition salts are acid salts such as the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embolic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For polynucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Regardless of the method by which the therapeutic agent of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:polynucleotide complexes of uncharacterized structure.

In one aspect, the pharmaceutical composition of the invention may be in the form of liposomes in which the synthetic polynucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in Szoka et al. (1980) Ann. Rev. Biophys. Bioeng. 9:467; U.S. Pat. Nos. 4,235,871, 4,501,728, and 4,837,028; the text Liposomes, Marc J. Ostro, ed., Chapter 1, Marcel Dekker, Inc., New York (1983), and Hope et al. (1986) Chem. Phys. Lip. 40:89.

Kits

All the essential materials for detecting, monitoring or treating ECA1 overexpression and for identifying anti-ECA1 therapeutic agents may be assembled in a kit or drug delivery system. One or more of the therapeutic or diagnostic agents, optionally in combination with other agents may be formulated into a single formulation or separate formulations. The kits may further comprise, or be packaged with, an instrument for assisting with the administration or placement of the formulation to a subject. Such an instrument may be an inhalant, syringe, pipette, forceps, measured spoon, eye dropper or any such medically approved delivery vehicle. Alternatively, the container means for the formulation may itself be an inhalant, syringe, pipette, eye dropper, or other like apparatus, from which the formulation may be administered or applied to the subject or mixed with the other components of the kit.

The components of the kit may be formulated in a variety of ways. For example, the components of the kit may be provided in one or more liquid solutions, the liquid solution preferably is an aqueous solution. The components of these kits may also be provided in dried or lyophilized forms. When reagents or components are provided as a dried form, reconstitution generally is by the addition of a suitable solvent, which may also be provided in another container means. In one aspect the polynucleotides of the invention may be formulated as liposomes by methods known in the art, as described herein.

The kits of the invention may also include an instruction sheet defining administration of the agents or methods for detecting neoplastic cells. The kits of the present invention also will typically include a means for containing the vials in close confinement for commercial sale such as, e.g., injection or blow-molded plastic containers into which the desired vials are retained. Other instrumentation includes devices that permit the reading or monitoring of reactions.

The following examples illustrate various aspects of the invention, but in no way are intended to limit the scope thereof.

Materials and Methods

Differential Display Reverse Transcriptase (DDRT). Paired tumor-normal samples of endometrial tissues to be analyzed by DDRT were prepared by examining the gross uterine specimen containing the tumor and carefully selecting uninvolved normal endometrial tissue and foci of endometrial carcinoma which were dissected, rapidly frozen liquid nitrogen, and examined histologically to confirm tissue homogeneity. DDRT was performed as described by Saffari (1998) (Pathobiology, Univ. Southern California, L.A., USA) (FIG. 1).

Northern Blot Analysis. In order to confirm the differential expression of cDNAs isolated by DDRT, 10 μg of total RNA isolated from fresh frozen specimens of normal ovary, endometrium at various phases of menstrual cycle, endometrial carcinomas, and ovarian tumors were subjected to Northern blot analysis as described in Saffari (1998) supra. Expression of ECA1 in normal human tissues (heart, brain, placenta, lung, liver, skeletal muscle, kidney, pancreas, spleen, thymus, prostate, testis, ovary, small intestine, colon) and peripheral blood leukocytes (CLONTECH, Palo Alto, Calif.) was evaluated with Northern blots containing 2 μg of Poly-A selected RNA and β-actin was used as an internal control gene as previously described in Saffari (1998) supra.

Isolation of ECA1 cDNA. Two approaches were utilized in cloning ECA1 cDNA. Rapid Amplification of cDNA Ends (RACE) utilizing the Marathon™ adapter-ligated human placenta cDNA library (CLONTECH, Alameda Calif.) was used (see Frohman, (1993) Methods Enz. 218:340-356) as described in Marathon™ cDNA amplification kit protocol and as described previously in Saffari (1998) supra. Since the ECA1 RACE product was smaller in size than the predicted ECA1 mRNA based on Northern blot analysis, a human placenta cDNA library in the λgt10 vector obtained from American Type Culture Collection (ATCC, Rockville, Md.) was screened with radiolabeled 5' RACE ECA1 clone for isolation of larger size cDNA clones. Approximately $2\times10^6$ clones were screened under stringent conditions and the hybridization positive clones were isolated, rescreened to ensure purity, and sequenced.

Isolation of ECA1 Genomic Clone. ECA1 genomic clones were isolated by screening a human bacterial artificial chromosome (BAC) genomic DNA library (Research Genetics, Huntsville Ala.) with an ECA1 probe (5' RACE-derived cDNA). BAC clones with strong hybridization signals were subjected to sequence analysis using ECA1-specific primers to confirm the identity of the genomic clones.

DNA Sequence Analysis. Both manual and ABI PRISM 373 automated DNA sequencing system (Applied Biosystems, Foster City, Calif.) were utilized for determination of ECA1 sequence. Both sense and antisense strands were sequenced. For manual sequencing, USB sequencing kit (Amersham, Arlington Heights, Ill.) was used. Sequence data were analyzed using the MacDNASIS sequence analysis software system (Hitachi, San Bruno, Calif.). To identify the putative ECA1 open reading frame, MacDNASIS and NCBI open reading frame (ORF) analysis programs were utilized. ECA1 cDNA and the deduced ECA1 amino acid sequence were compared to GenBank™ (the NIH genetic sequence database, an annotated collection of all publicly available DNA sequences), and EMBL DNA and protein databases for homology determinations using the Blast search programs as described in Altschul et al. (1997) Nucl. Acids Res. 25:3389-

3402. Prosite was used for determination of consensus sequences and pfam was used for the identification of conserved protein domains.

Fluorescence in situ Hybridization (FISH). FISH was used to identify the chromosomal localization of ECA1 as described previously in Saffari, (1998) supra.

Southern Blot Analysis. A Southern blot filter containing 4 μg of EcoR I-digested genomic DNA from different eukaryotic species {human, monkey (Rhesus), rat (Sprague-Dawley), mouse (BALB/c), dog, bovine, rabbit, chicken and yeast (Saccharomyces cerevisiae)} (CLONTECH, Alameda Calif.) was probed with radiolabled ECA1 probe (RACE-derived cDNA). The source of genomic DNA in human was placenta; in chicken, the liver; and in the remaining mammals, the kidney.

Detection and Isolation of ECA1 partial cDNA Among Differentially Expressed mRNAs in Endometrial Carcinoma. To detect and isolate genes differentially expressed in endometrial carcinoma, the expression pattern of genes in human proliferative endometrium was compared with the pattern in endometrial carcinoma by DDRT. Among the PCR amplified cDNA fragments, a partial cDNA amplified by using the primer pair (dT)12VG (TTTTTTTTTTTTTVG) (SEQ ID NO.: 3) and OP-DDRT1 (TACAACGAGG) (SEQ ID NO.: 4) was expressed in endometrial carcinoma but not identified in normal proliferative endometrial mRNA (FIG. 1). The partial cDNA recovered from the DDRT gel was reamplified using the same primer pair as above and cloned into a TA cloning vector. The partial cDNA was 215 base pairs in length.

Isolation and Characterization of ECA1 cDNA. An ECA1 cDNA (988 nucleotides long) was obtained using an adaptor-ligated placenta cDNA library and RACE as described in Saffari (1998) supra. Since this cDNA was significantly shorter than the expected size of ECA1 mRNA as revealed by Northern blot analysis, another approach was used to isolate full-length ECA1 cDNA. The RACE-derived ECA1 cDNA was used as a probe to screen a human placental cDNA library. This strategy yielded a cDNA 1830 nucleotides-long (including a 28 nucleotides poly-A tail) which contained the entire open reading frame of ECA1.

Identification of Sequences with Significant Homology to ECA1. The nucleotide sequence homology search of GenBank™ (the NIH genetic sequence database, an annotated collection of all publicly available DNA sequences) database identified two essentially identical genes, "LOC147111" and "OK/SW-CL.30". LOC147111 is a predicted gene located on chromosome 17q25.3. Its mRNA sequence was predicted from NCBI contig NT 010845 by automated computational analysis using gene prediction method (NCBI Annotation Project) and the predicted sequence was further supported by EST data. "OK/SW-CL.30" is a tumor antigen recognized by tumor infiltrating cytotoxic T lymphocytes of colon cancer patients. Its cDNA was isolated from SW620 colon carcinoma cell line. (Accession no. ABO62438). DNA sequence homology search of GenBank EST database with ECA1 cDNA yielded nearly identical matching cDNAs found in placenta, pregnant uterus, pooled fetal liver/spleen, fetal lung cDNA libraries as well as cDNA clones generated from small cell carcinoma of the lung, metastatic chondrosarcoma, colon carcinoma and seven pooled well differentiated adenocarcinomas.

Deduced Genomic Structure of ECA1 and Identification of Single Nucleotide Polymorphisms. By comparing the ECA1 cDNA sequence to the genomic DNA sequence obtained from GenBank™ (the NIH genetic sequence database, an annotated collection of all publicly available DNA sequences) database and employing the 'AG-GT' rule to predict the exon/intron splice sites, the possible genomic organization of ECA1 ("LOC147111") was elucidated which is confirmed by the human genome annotation project (as of May 13, 2002). ECA1 was found to contain 11 exons and 10 introns (FIG. 1B). ECA1 gene locus harbors two intronic single nucleotide polymorphisms (T/A substitution) on contig NT 010845 at positions 175821 in intron IX, and position 178556 in intron VI. Furthermore, this cDNA sequence differs from LOC147111. There is a G for T substitution at position 174298 in exon X on contig NT 010845 resulting in a change in amino acid from valine to leucine (see FIG. 2A).

Deduced Amino [AcidSequence] *Acid Sequence* of ECA1 and Putative Consensus Sequences. The deduced amino acid sequence of ECA1 is shown in FIG. 3. ECA1 encodes a 434 amino acid-long protein with a predicted molecular weight of approximately 49 kDa. The ECA1 deduced amino acid sequence differs from LOC147111 predicted protein sequence at amino acid 340. ECA1 encodes a valine and LOC147111 encodes a leucine. This difference in sequence of a conserved amino acid is predicted to represent a polymorphism. OK/SW-CL.30 predicted amino acid sequence is identical to ECA1 and LOC147111 but it is eighty amino acids shorter at the N-terminus and it uses the methionine at position 81 for initiation of translation. Similar to ECA1, it encodes a leucine at amino acid position 340. ECA1 encoded protein is rich in serine/threonine amino acid residues with nine consensus protein kinase C (PKC) phosphorylation sites, nine casein kinase II (CK-2) phosphorylation sites, and a tyrosine kinase phosphorylation site (see FIG. 3). ECA1 also harbors bipartite nuclear targeting sequence 17 amino acids long from amino acid 230 to 246 (see FIG. 3). ECA1 also contains nine N-myristoylation consensus sites but none are located at the N-terminus. A glycine residue at position 42 may potentially become myristoylated if additional N-terminus posttranslational processing occurs. ECA1 also has a putative N-glycosylation site, Asn 34 (see FIG. 3).

ECA1 Encodes a Protein Highly Homologous to a Protein Involved in Drosophila melanogaster Wing Development with Structural Similarity to Pectin Acetylesterase. ECA1 deduced amino acid sequence is significantly homologous to wingful also known as Notum protein of Drosophila [melonogaster] *melanogaster* (FIG. 4A) and agCP6173 predicted protein of Anopheles gambiae. In the region with a high degree of alignment, as shown in FIG. 4A, ECA1 has a 46% sequence identity and a 63% sequence homology with wingful/Notum protein. Similarly, ECA1 has a 43% sequence identity and a 63% sequence homology with an Anopheles gambiae hypothetical protein. The conserved domain homology search using [pfam] *Pfam* revealed 63.5% alignment to pectin acetylesterase (PAE) in the 244 amino acids long region, see FIG. 4C. Similar to wingful/Notum and PAE, ECA1 harbors the α/β hydrolase consensus active site motif G-X-S-X-G (see FIG. 3) also known as "nucleophile elbow" (Nardine et al. (1999) Curr. Opin. Struct. Biol. 9:732-737). The conserved Ser 170 of the nucleophile elbow, in addition to Asp 278 and His 327 equivalents in wingful/Notum are predicted to form the catalytic active sites (see Giraldez, et al. (2002) Dev. Cell. 5:667-676).

Overexpression of ECA1 in Endometrioid-type Carcinomas of Endometrium and Ovary. Northern blot analysis was performed to examine the expression of ECA1 in sporadic endometrial carcinomas as well as proliferative, secretory and atrophic-endometrium (see FIG. 4). ECA1 mRNA was not detected in normal endometrium however, 5 of 9 sporadic endometrial carcinomas showed ECA1 expression. ECA1 was not uniformly expressed among the five tumors showing ECA1 expression. Three endometrial carcinomas showed low levels, one showed moderate levels and one showed high levels of ECA1 mRNA expression as assessed by Northern blot. Similarly, both normal ovary and a series of ovarian tumors of different histologic-type were examined for expression of ECA1 by Northern blot analysis. ECA1 was highly expressed in 2 of 4 endometrioid-type ovarian carcinomas. ECA1 mRNA was not detected in a normal ovary, a benign Brenner type ovarian tumor, a sarcoma, a clear-cell carcinoma or in 9 serous-cell ovarian carcinomas.

Figure 7:
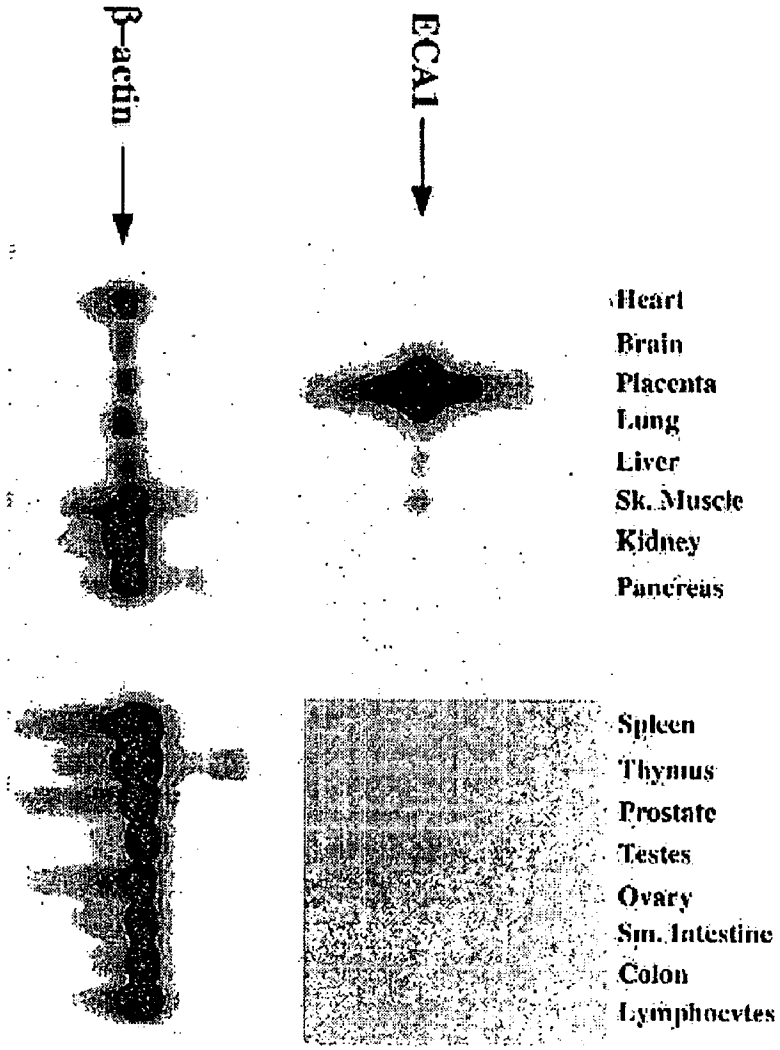
FIG. 7. Expression of ECA1 in normal human tissues. Poly-A selected RNA (2 μg per lane) from multiple human tissues including placenta, ovary and peripheral blood leukocytes were examined for expression of ECA1 by Northern blot analysis using a partial ECA1 cDNA as a probe (top panel, exposed to radiographic film for 13 days). For comparison the expression of β-actin was also examined in these samples (lower panel, 16 hrs exposure). A strong hybridization signal corresponding to approximately 2.4 kb transcript is identified in placenta whereas liver, skeletal muscle and testis show a barely detectable signal even after 13 days of exposure (top panel). No expression was detected in ovary, heart, brain, lung, kidney, pancreas, spleen, thymus, prostate, small intestine, colon and peripheral blood leukocytes. On the other hand, β-actin is moderately to highly expressed in all samples (lower panel).

High-levels of ECA1 mRNA in Placenta and the Lack of Expression in the Majority of Normal Human Adult Tissues. Poly-A selected RNA from multiple human adult tissues and placenta were examined for expression of ECA1 mRNA. Only placenta expressed significant levels of ECA1 mRNA and this expression was very high (see FIG. 7). In contrast, among adult tissues only skeletal muscle, liver, and testis showed detectable, low levels of ECA1 mRNA as demonstrated by weak signals on poly-A selected Northern blot exposed for a period of 13 days. No expression was detected in heart, brain, lung, kidney, pancreas, spleen, thymus, prostate, ovary, small intestine, colon and peripheral blood leukocytes. (see FIG. 7).

Figure 8:
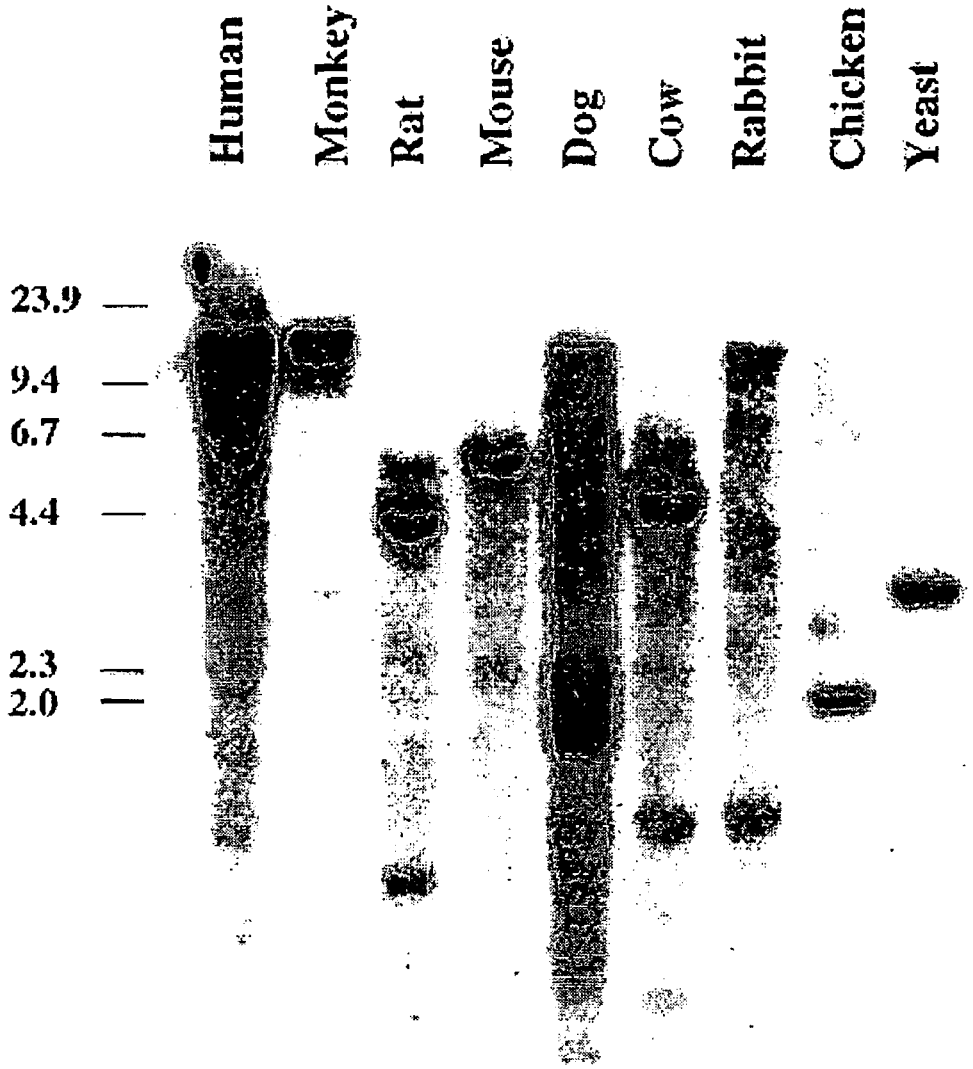
FIG. 8. Detection of ECA1 gene in DNA of simple and complex eukaryotic organisms. A premade zoo-blot containing 4 μg of EcoR I-digested genomic DNA from human, Rhesus monkey, Sprague-Dawley rat, BALB/c mouse, dog, bovine, rabbit, chicken and yeast Saccharomyces cerevisiae was hybridized with radiolabeled ECA1 cDNA under stringent conditions. Strong hybridization signals are detected in all organisms. One major band approximately 20 kb in size are identified in human and monkey DNA. A similar sized band (18 kb) is identified in dog and rabbit. The major hybridization signals detected in rat, mouse, cow and chicken are 4.4 kb, 6.5 kb, 5 kb, and 2.2 kb in size, respectively. A strong hybridization signal is detected in yeast Saccharomyces cerevisiae measuring 4 kb in size.

Possible Conservation of ECA1 Gene Among Simple and Complex Eukaryotic Organisms. Southern blot analysis of DNA derived from human, monkey, rat, mouse, rabbit, cow, dog, chicken, and yeast was performed using 5' RACE ECA1 cDNA fragment under stringent hybridization conditions to determine whether ECA1 is evolutionarily conserved among eukaryotic organisms (see FIG. 8). Strong hybridization signals were detected in all organisms. The assertion that ECA1 is evolutionarily conserved is further supported by identification of a highly homologous cDNA clone found in an 8-day-old mouse embryo cDNA library, a highly homologous cow cDNA and ECA1 significant amino acid sequence homology to wingful/Notum.

Figure 9:
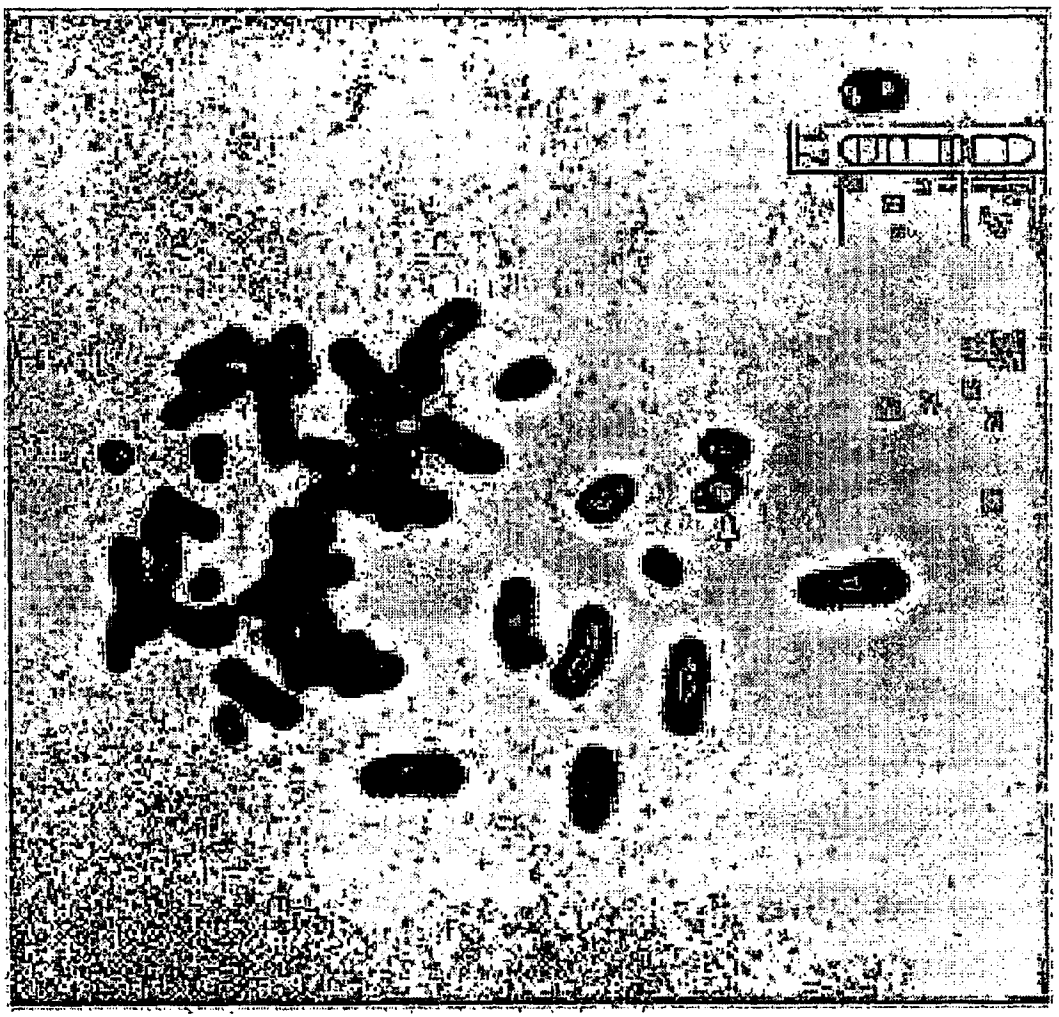
FIG. 9. Chromosomal localization of ECA1 by fluorescent in situ hybridization. Biotin-labeled ECA1 genomic clone was hybridized to the metaphase chromosome spread of male human lymphocyte. ECA1 is localized to the distal end of the long arm (q25) of chromosome 17, shown as green fluorescent signals. The arrows indicate the location of chromosome 17-specific alpha satellite centromere probe, shown as light grey fluorescent signals. The schematic diagram of chromosome 17 is shown for reference next to a fluorescent labeled chromosome 17.

Localization of ECA1 to the Distal End of the Long Arm of Chromosome 17 (17q25.3). Fluorescent labeled ECA1 genomic clone was used to identify the location of ECA1 gene on twenty metaphase chromosome spreads of human lymphocytes. The gene was localized to the telomeric region of the long arm of chromosome 17q25.3, shown as two fluorescent signals (FIG. 9) on the telomeric region of the long arm of chromosome 17. In a dual fluorescent labeling experiment, the location of ECA1 to chromosome 17 was confirmed by colocalization of a chromosome 17-specific alpha satellite centromere probe, and ECA1 genomic cosmid probe (FIG. 9). The localization of ECA1 is confirmed by sequence analysis of the human genome database.

Identification Of Putative TCF/Lymphocyte Enhancing Factor (LEF) DNA Binding Sites In ECA1 Promoter Region. The putative promoter region of ECA1 (5' flanking region of LOC147111, GI: 22064811) was examined for the presence of putative TCF/LEF DNA binding sites. Three putative TCF/LEF consensus DNA binding sites (5'-[T/A][T/A]CAAAG-3') (SEQ ID. NO.: 5) were identified. ECA1 also harbors a pair of identical 15 base-pair long (5'-TCC CAAAGTGCTG-3') (SEQ ID NO.: 6) elements in the promoter region, which contain a portion of putative TCF/LEF DNA binding sequence (underlined).

DISCUSSION

Comparative gene expression strategies are powerful tools to identify and isolate genes associated with gynecologic malignancies. DDRT was used to identify genes selectively up regulated in endometrial cancer relative to proliferative endometrium.

ECA1 showed an expression pattern limited to endometrioid carcinomas and normal placenta. ECA1 was overexpressed in about 50% of endometrioid-type carcinomas of ovary and endometrium. Furthermore, benign ovarian tumors, clear-cell carcinoma, serous-cell carcinoma and mucinous ovarian carcinomas lacked ECA1 expression.

Similar to many proto-oncogenes, ECA1 was highly expressed in malignant tissues but was not expressed in the normal tissue counterpart. ECA1 expression was not detected in normal proliferative endometrium by Northern blot analysis and RT-PCR, however EST database does indicate that ECA1 cDNA is detected in pregnant uterus. Likewise ECA1 mRNA was not detected in normal ovary by Northern blot analysis of total and poly-A selected RNA. The only normal adult tissue with substantial expression of ECA1 was placenta. Two essential characteristics of malignancy, tissue invasion and induction of de novo angiogenesis, are features shared with placenta. Moreover, ECA1 also may be expressed in other types of malignancies including colon carcinoma, small cell lung carcinoma and metastatic chondrosarcoma based on GenBank™ EST database (the NIH genetic sequence database, an annotated collection of all publicly available DNA sequences). This notion is further supported by the fact that ECA1 is essentially identical to a colon carcinoma tumor antigen (OK/SW-CL.30) recognized by infiltrating cytotoxic T lymphocytes suggesting a possible role in other malignancies.

The OK/SW-CL.30 cDNA is 124 base pairs shorter than ECA1 cDNA and it appears to lack a portion of exon I harboring the initiation codon and the predicted amino acid sequence is identical to ECA1 but it is eighty amino acids shorter at the N-terminus and it is predicted to use codon 81 for initiation of translation. Since OK/SW-CL.30 cDNA is obtained from colon adenocarcinoma one may speculate that OK/SW-CL.30 may represent a "truncated" ECA1 with possible altered function.

The predicted ECA1-encoded protein contains multiple PKC phosphorylation sites, CK-2 phosphorylation sites and a tyrosine kinase phosphorylation site suggesting participation in signal transduction. Protein kinase C appears to mediate the mitogenic activity of epidermal growth factor in endometrial cancer (Connor (1997) Gynecol. Oncol. 67:46-50) and the mitogenic activity of endothelin 1 in ovarian cancer (Bagnato et al. (1997) Cancer Res. 57:1306-1311). There are multiple myristoylation consensus sequences in ECA1 but none are located at the N-terminus. A glycine residue at position 42 may potentially become myristoylated if additional N-terminus posttranslational processing occurs. ECA1 also harbors a nuclear targeting sequence suggesting possible function within the nucleus; however, similar to wingful/Notum, ECA1 may harbor a putative signal sequence in the N-terminus. ECA1 also has a putative N-glycosylation site at Asn 34.

Given the conservation of canonical Wingless/Wnt signal transduction pathway between Drosophila and vertebrates and ECA1 high degree of homology with wingful/Notum, in one aspect, this invention provides methods to mediate comparable functions to Wingless/Wnt activity. The Wnt/Wingless pathway is evolutionarily conserved among Drosophila and vertebrates (Cadigan et al. (1997) Genes Dev. 11:3286-3305 and Morin (1999) Bio Essays 21:1021-1030). This pathway plays a key role in embryogenesis, morphogenesis and organ development (Cadigan et al. (1990) supra) including female reproductive tract (Heikkila et al. (2001) J. Exp. Zoology 290:616-623). Multiple Wnt signaling pathways have been identified (Peifer et al. (2002) Cell 109:271-274). In the canonical Wnt signaling pathway, Wnt/Wingless interacts with its transmembrane receptor Frizzled which in turn activates Disheveled. Disheveled down-regulates the activity of Shaggy/GSK3β (glycogen synthase kinase 3β) ultimately resulting in stabilization of cytoplasmic β-catenin/Armadillo. β-catenin forms a complex with the TCF and LEF family of transcription factors (Clevers et al. (1997) TIG 13:485-489) to induce expression of target genes including cyclin D1

(Shtutman et al. (1999) PNAS 96:5522-5527), c-MYC (He et al. (1998) Science 281:1509-1512), and MMP-7 (Crawford et al. (1999) Oncogenes 18:2883-2891). In malignancy, β-catenin may become stabilized and activated as a result of mutations in adenomatous polyposis coli (APC) (Fujita, M. et al. (1995) Int. J. Cancer 64:361-366), AXIN I (King, B. L. et al. (1995) Br. J. Cancer 72:376-382), or AXIN II (Risinger, J. I., et al. (1993) Cancer Res. 53:5100-5103), which normally form a complex with β-catenin and target it for phosphorylation and destruction. β-catenin becomes stable as a result of mutations in β-catenin [scrine] *serine*/threonine phosphorylation sites preventing its phosphorylation by GSK3β (Cheng, J. Q. et al. (1992) PNAS 89:9267-9271 and Fujita, M. et al. (1995) supra) and degradation by proteasome. Membrane-bound HSPGs have also been found to mediate the activity of Wnt/Wingless signaling cascade (Palacios, J. & Gamallo, C. (1998) 58:1344-1347; and Fukuchi, T. et al. (1998) 58:3526-3528) and these molecules play a significant role in malignant phenotype (Saegusa, M. & Okayasu, I. (2001) J. Pathol. 194:59-67).

Figure 10:
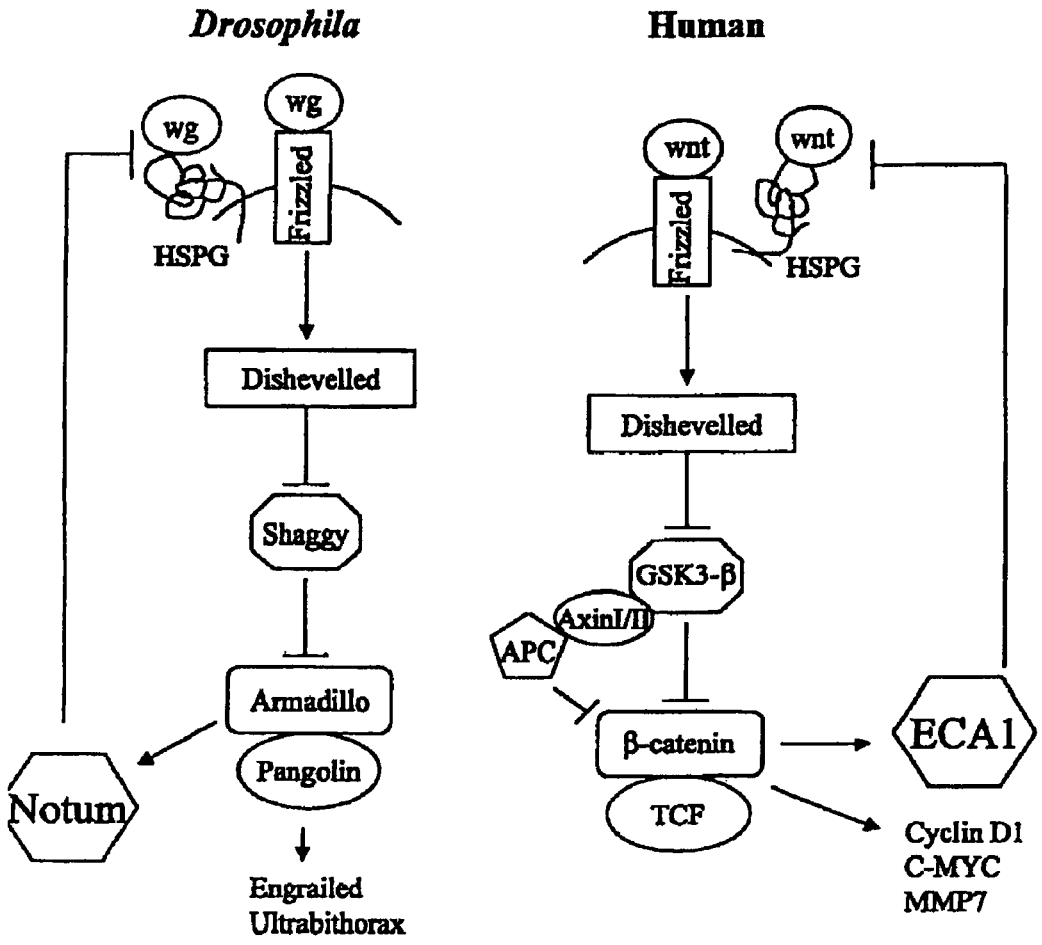
FIG. 10. Proposed model of ECA1 in the Wnt signaling pathway.

A proposed model of the ECA1 role in the Wnt pathway is shown in FIG. 10. ECA1 can function as a target of β-catenin/TCF transcription complex. ECA1 promoter region which contains three putative TCF/LEF consensus DNA binding sites. Furthermore, wingful/Notum expression was induced by ectopic expression of constitutively active armadillo, the β-catenin homolog in Drosophila (Link, C. et al. (1996) Gynecol. Oncol. 60:347-354). In carcinomas with β-catenin deregulation including the endometrioid-type uterine and ovarian carcinomas, a substantial proportion are expected to show ECA1 overexpression. Interestingly, approximately 40% of ovarian endometrioid carcinomas show β-catenin deregulation (Wu, R. et al. (2001) Cancer Res. 61:8247-8255), which is similar to the percentage of cases with ECA1 overexpression reported in this study. Based on the structural similarity of wingful/Notum to α/β hydrolase family of enzymes and the ability of wildtype and not the mutant wingful/Notum to modify the Drosophila glypicans Dally and Dally-like based on immunoblots, it has been suggested that wingful/Notum may act as an hydrolase by removing the acetyl groups from N-acetylglucosamine of glycosoaminoglycans (Link, C. J. et al. (1996) supra). Moreover, the phylogenetic analysis of the predicted mouse and human proteins homologous to wingful/Notum by Giraldez et al. has revealed that these genes are orthologs with likely similar functions (Link, C. J. et al. (1996) supra). Thus, ECA1 also modulates the Wnt activity and contribute to malignant phenotype by enzymatically modifying the HSPGs. Interestingly, the expression of GPC3, a member of glypican family, is lost in a large number of ovarian cancer cell lines possibly as a result of hypermethylation of promoter elements and ectopic expression of GPC3 reduces the colony-forming activity in these cell lines (Moreno-Bueno, G. et al. (2001) Diag. Mol. Path. 10:116-122).

SEQUENCE LISTING

```
<160> NUMBER OF SEQ ID NOS: 13

<210> SEQ ID NO 1
<211> LENGTH: 434
<212> TYPE: PRT
<213> ORGANISM: Homo sapiens

<400> SEQUENCE: 1

Met Asp Ser Phe Met Ala Gln Val Lys Ser Leu Ala Gln Ser Leu Tyr
 1               5                  10                  15

Pro Cys Ser Ala Gln Gln Leu Asn Glu Asp Leu Arg Leu His Leu Leu
            20                  25                  30

Leu Asn Thr Ser Val Thr Cys Asn Asp Gly Ser Pro Ala Gly Tyr Tyr
        35                  40                  45

Leu Lys Glu Ser Arg Gly Ser Arg Arg Trp Leu Leu Phe Leu Glu Ala
    50                  55                  60

Val Trp Tyr Cys Phe Asn Arg Glu Asn Cys Asp Ser Arg Tyr Asp Thr
65                  70                  75                  80

Met Arg Arg Leu Met Ser Ser Arg Asp Trp Pro Arg Thr Arg Thr Gly
                85                  90                  95

Thr Gly Ile Leu Ser Ser Gln Pro Glu Glu Asn Pro Tyr Trp Trp Asn
            100                 105                 110

Ala Asn Met Val Phe Ile Pro Tyr Cys Ser Ser Asp Val Trp Ser Gly
        115                 120                 125

Ala Ser Ser Lys Ser Glu Lys Asn Glu Tyr Ala Phe Met Gly Ala Leu
    130                 135                 140

Ile Ile Gln Glu Val Val Arg Glu Leu Leu Gly Arg Gly Leu Ser Gly
145                 150                 155                 160

Ala Lys Val Leu Leu Leu Ala Gly Ser Ser Ala Gly Gly Thr Gly Val
                165                 170                 175

Leu Leu Asn Val Asp Arg Val Ala Glu Gln Leu Glu Lys Leu Gly Tyr
```

```
            180                 185                 190

Pro Ala Ile Gln Val Arg Gly Leu Ala Asp Ser Gly Trp Phe Leu Asp
        195                 200                 205

Asn Lys Gln Tyr Arg His Thr Asp Cys Val Asp Thr Ile Thr Cys Ala
    210                 215                 220

Pro Thr Glu Ala Ile Arg Arg Gly Ile Arg Tyr Trp Asn Gly Val Val
225                 230                 235                 240

Pro Glu Arg Cys Arg Arg Gln Phe Gln Glu Gly Glu Glu Trp Asn Cys
                245                 250                 255

Phe Phe Gly Tyr Lys Val Tyr Pro Thr Leu Arg Cys Pro Val Phe Val
            260                 265                 270

Val Gln Trp Leu Phe Asp Glu Ala Gln Leu Thr Val Asp Asn Val His
        275                 280                 285

Leu Thr Gly Gln Pro Val Gln Glu Gly Leu Arg Leu Tyr Ile Gln Asn
    290                 295                 300

Leu Gly Arg Glu Leu Arg His Thr Leu Lys Asp Val Pro Ala Ser Phe
305                 310                 315                 320

Ala Pro Ala Cys Leu Ser His Glu Ile Ile Ile Arg Ser His Trp Thr
                325                 330                 335

Asp Val Gln Leu Lys Gly Thr Ser Leu Pro Arg Ala Leu His Cys Trp
            340                 345                 350

Asp Arg Ser Leu His Asp Ser His Lys Ala Ser Lys Thr Pro Leu Lys
        355                 360                 365

Gly Cys Pro Val His Leu Val Asp Ser Cys Pro Trp Pro His Cys Asn
    370                 375                 380

Pro Ser Cys Pro Thr Val Arg Asp Gln Phe Thr Gly Gln Glu Met Asn
385                 390                 395                 400

Val Ala Gln Phe Leu Met His Met Gly Phe Asp Met Gln Thr Val Ala
                405                 410                 415

Gln Pro Gln Gly Leu Glu Pro Ser Glu Leu Leu Gly Met Leu Ser Asn
            420                 425                 430

Gly Ser


<210> SEQ ID NO 2
<211> LENGTH: 1829
<212> TYPE: DNA
<213> ORGANISM: Homo sapiens

<400> SEQUENCE: 2

cggccggaca gcccgtggag agcttcccgc tggacttcac ggccgtggag ggtaacatgg      60

acagcttcat ggcgcaagtc aagagcctgg cgcagtccct gtacccctgc tccgcgcagc     120

agctcaacga ggacctgcgc ctgcacctcc tactcaacac ctcggtgacc tgcaacgacg     180

gcagccccgc cggctactac ctgaaggagt ccaggggcag ccggcggtgg ctcctcttcc     240

tggaagccgt ctggtactgc ttcaaccgcg agaactgcga ctccagatac gacaccatgc     300

ggcgcctcat gagctcccgg gactggccgc gcactcgcac aggcacaggg atcctgtcct     360

cacagccgga ggagaacccc tactggtgga acgcaaacat ggtcttcatc ccctactgct     420

ccagtgatgt ttggagcggg gcttcatcca agtctgagaa gaacgagtac gccttcatgg     480

gcgccctcat catccaggag gtggtgcggg agcttctggg cagagggctg agcggggcca     540

aggtgctgct gctggccggg agcagcgcgg ggggcaccgg ggtgctcctg aatgtggacc     600

gtgtggctga gcagctggag aagctgggct acccagccat ccaggtgcga ggcctggctg     660

actccggctg gttcctggac aacaagcagt atcgccacac agactgcgtc gacacgatca     720
```

```
cgtgcgcgcc cacggaggcc atccgccgtg gcatcaggta ctggaacggg gtggtcccgg    780

agcgctgccg acgccagttc caggagggcg aggagtggaa ctgcttcttt ggctacaagg    840

tctacccgac cctgcgctgc cctgtgttcg tggtgcagtg gctgtttgac gaggcacagc    900

tgacggtgga caacgtgcac ctgacggggc agccggtgca ggagggcctg cggctgtaca    960

tccagaacct cggccgcgag ctgcgccaca cactcaagga cgtgccggcc agctttgccc   1020

ccgcctgcct ctcccatgag atcatcatcc ggagccactg gacggatgtc caggtgaagg   1080

ggacgtcgct gccccgagca ctgcactgct gggacaggag cctccatgac agccacaagg   1140

ccagcaagac ccccctcaag ggctgccccg tccacctggt ggacagctgc ccctggcccc   1200

actgcaaccc ctcatgcccc accgtccgag accagttcac ggggcaagag atgaacgtgg   1260

cccagttcct catgcacatg ggcttcgaca tgcagacggt ggcccagccg cagggactgg   1320

agcccagtga gctgctgggg atgctgagca acggaagcta ggcagactgt ctggaggagg   1380

agccggcact gaggggccca gacacccgct gcaccagtgc cacctcaccc cacaccagca   1440

ggccctcccg tctcttcggg acagggcacc agccgtcccc cctgtctggg tatgctcact   1500

gccctcctgc cccggctttc cctgcccctc tcccacagcc cagccagaga caagggacct   1560

gctgtcatcc ccatctgtgg cctgggggtc cttcctgaca acgagggggt agccagaaga   1620

gaagcactgg attcctcagt ccaccagctc agacagcacc caccggcccc acccatcaag   1680

ccctttttata ttattttata aagtgacttt tttattactt taatttttta aaaaaaggaa   1740

aataagaata tatgatgaat gatattgttt tgtaactttt taaaaatgat tttaaagaga   1800

caaaaaaaaa aaaaaaaaaa aaaaaaaaa                                     1829
```

<210> SEQ ID NO 3
<211> LENGTH: 14
<212> TYPE: DNA
<213> ORGANISM: Homo sapiens

<400> SEQUENCE: 3

```
tttttttttt ttvg                                                       14
```

<210> SEQ ID NO 4
<211> LENGTH: 10
<212> TYPE: DNA
<213> ORGANISM: Homo sapiens

<400> SEQUENCE: 4

```
tacaacgagg                                                            10
```

<210> SEQ ID NO 5
<211> LENGTH: 7
<212> TYPE: DNA
<213> ORGANISM: Homo sapiens
<220> FEATURE:
<221> NAME/KEY: misc_binding
<222> LOCATION: (1)...(7)
<223> OTHER INFORMATION: TCF/LEF consensus DNA binding sites

<400> SEQUENCE: 5

```
wwcaaag                                                                7
```

<210> SEQ ID NO 6
<211> LENGTH: 13
<212> TYPE: DNA
<213> ORGANISM: Homo sapiens
<220> FEATURE:
<221> NAME/KEY: misc_binding <222> LOCATION: (1)...(13)
<223> OTHER INFORMATION: ECA1 also harbors a pair of identifical 15 base pair line elements in the promoter region, which contains a portion of the putative TCF/LEF binding sequence.
<220> FEATURE:
<221> NAME/KEY: misc_binding
<222> LOCATION: (4)...(8)
<223> OTHER INFORMATION: TCF/LEF DNA binding sequence

<400> SEQUENCE: 6 tcccaaagtg ctg 13

<210> SEQ ID NO 7
<211> LENGTH: 5
<212> TYPE: PRT
<213> ORGANISM: Homo sapiens
<220> FEATURE:
<221> NAME/KEY: VARIANT
<222> LOCATION: 2, 4
<223> OTHER INFORMATION: Xaa = Any Amino Acid

<400> SEQUENCE: 7

Gly Xaa Ser Xaa Gly
1 5

<210> SEQ ID NO 8
<211> LENGTH: 407
<212> TYPE: PRT
<213> ORGANISM: Homo sapiens

<400> SEQUENCE: 8

Leu Leu Asn Thr Ser Val Thr Cys Asn Asp Gly Ser Pro Ala Gly Tyr
1 5 10 15

Tyr Leu Lys Glu Ser Arg Gly Ser Arg Arg Trp Leu Leu Phe Leu Glu
20 25 30

Ala Val Trp Tyr Cys Phe Asn Arg Glu Asn Cys Asp Ser Arg Tyr Asp
35 40 45

Thr Met Arg Arg Leu Met Ser Ser Arg Asp Trp Pro Arg Thr Arg Thr
50 55 60

Gly Thr Gly Ile Leu Ser Ser Gln Pro Glu Glu Asn Pro Tyr Trp Trp
65 70 75 80

Asn Ala Asn Met Val Phe Ile Pro Tyr Cys Ser Ser Asp Val Trp Ser
85 90 95

Gly Ala Ser Ser Lys Ser Glu Lys Asn Glu Tyr Ala Phe Met Gly Ala
100 105 110

Leu Ile Ile Gln Glu Val Val Arg Glu Leu Leu Gly Arg Gly Leu Ser
115 120 125

Gly Ala Lys Val Leu Leu Leu Ala Gly Ser Ser Ala Gly Gly Thr Gly
130 135 140

Val Leu Leu Asn Val Asp Arg Val Ala Glu Gln Leu Glu Lys Leu Gly
145 150 155 160

Tyr Pro Ala Ile Gln Val Arg Gly Leu Ala Asp Ser Gly Trp Phe Leu
165 170 175

Asp Asn Lys Gln Tyr Arg His Thr Asp Cys Val Asp Thr Ile Thr Cys
180 185 190

Ala Pro Thr Glu Ala Ile Arg Arg Gly Ile Arg Tyr Trp Asn Gly Val
195 200 205

Val Pro Glu Arg Cys Arg Arg Gln Phe Gln Glu Gly Glu Glu Trp Asn
210 215 220

Cys Phe Phe Gly Tyr Lys Val Tyr Pro Thr Leu Arg Cys Pro Val Phe

```
225                 230                 235                 240

Val Val Gln Trp Leu Phe Asp Glu Ala Gln Leu Thr Val Asp Asn Val
                245                 250                 255

His Leu Thr Gly Gln Pro Val Gln Glu Gly Leu Arg Leu Tyr Ile Gln
            260                 265                 270

Asn Leu Gly Arg Glu Leu Arg His Thr Leu Lys Asp Val Pro Ala Ser
        275                 280                 285

Phe Ala Pro Ala Cys Leu Ser His Glu Ile Ile Ile Arg Ser His Trp
    290                 295                 300

Thr Asp Val Gln Leu Lys Gly Thr Ser Leu Pro Arg Ala Leu His Cys
305                 310                 315                 320

Trp Asp Arg Ser Leu His Asp Ser His Lys Ala Ser Lys Thr Pro His
                325                 330                 335

Lys Ala Ser Lys Thr Pro Leu Lys Gly Cys Pro Val His Leu Val Asp
            340                 345                 350

Ser Cys Pro Trp Pro His Cys Asn Pro Ser Cys Pro Thr Val Arg Asp
        355                 360                 365

Gln Phe Thr Gly Gln Glu Met Asn Val Ala Gln Phe Leu Met His Met
    370                 375                 380

Gly Phe Asp Met Gln Thr Val Ala Gln Pro Gln Gly Leu Glu Pro Ser
385                 390                 395                 400

Glu Leu Leu Gly Met Leu Ser
                405


<210> SEQ ID NO 9
<211> LENGTH: 414
<212> TYPE: PRT
<213> ORGANISM: Homo  sapiens

<400> SEQUENCE: 9

Leu Ala Asn Thr Ser Ile Thr Cys Asn Asp Gly Ser His Ala Gly Phe
 1               5                  10                  15

Tyr Leu Arg Lys His Pro Ser Ser Lys Lys Trp Ile Val Leu Leu Glu
            20                  25                  30

Gly Gly Trp His Cys Phe Asp Val Arg Ser Cys Arg Ser Arg Trp Met
        35                  40                  45

Arg Leu Arg His Leu Met Thr Ser Ser Gln Trp Pro Glu Thr Arg Asp
    50                  55                  60

Val Gly Gly Ile Leu Ser Pro His Pro Glu Glu Asn Pro Tyr Trp His
65                  70                  75                  80

Asn Ala Asn His Val Leu Ile Pro Tyr Cys Ser Ser Asp Ser Trp Ser
                85                  90                  95

Gly Thr Arg Thr Glu Pro Asp Thr Ser Asp Arg Glu Asn Ser Trp Arg
            100                 105                 110

Phe Met Gly Ala Leu Ile Leu Arg Gln Val Ile Ala Glu Leu Ile Pro
        115                 120                 125

Val Gly Leu Gly Arg Val Pro Gly Gly Glu Leu Met Leu Val Gly Ser
    130                 135                 140

Ser Ala Gly Gly Met Gly Val Met Leu Asn Leu Asp Arg Ile Arg Asp
145                 150                 155                 160

Phe Leu Val Asn Glu Lys Lys Leu Gln Ile Thr Val Arg Gly Val Ser
                165                 170                 175

Asp Ser Gly Trp Phe Leu Asp Arg Glu Pro Tyr Thr Pro Ala Ala Val
            180                 185                 190

Ala Ser Asn Glu Ala Val Arg Gln Gly Trp Lys Leu Trp Gln Gly Leu
```

```
        195                 200                 205

Leu Pro Glu Glu Cys Thr Lys Ser Tyr Pro Thr Glu Pro Trp Arg Cys
    210                 215                 220

Tyr Tyr Gly Tyr Arg Leu Tyr Pro Thr Leu Lys Thr Pro Leu Phe Val
225                 230                 235                 240

Phe Gln Trp Leu Phe Asp Glu Ala Gln Met Arg Val Asp Asn Val Gly
                245                 250                 255

Ala Pro Val Thr Pro Gln Gln Trp Asn Tyr Ile His Glu Met Gly Gly
            260                 265                 270

Ala Leu Arg Ser Ser Leu Asp Asn Val Ser Ala Val Phe Ala Pro Ser
        275                 280                 285

Cys Ile Gly His Gly Val Leu Phe Lys Arg Asp Trp Val Asn Ile Lys
    290                 295                 300

Ile Asp Asp Ile Ser Leu Pro Ser Ala Leu Arg Cys Trp Glu His Ser
305                 310                 315                 320

Thr Arg Ser Arg Arg His Asp Lys Leu Lys Arg Ser Thr Glu Pro His
                325                 330                 335

Arg Val Pro Arg Val Pro Glu Lys Cys Gly Leu Arg Leu Leu Glu Arg
            340                 345                 350

Cys Ser Trp Pro Gln Cys Asn His Ser Cys Pro Thr Leu Thr Asn Pro
        355                 360                 365

Met Thr Gly Glu Glu Met Arg Phe Leu Glu Leu Leu Thr Ala Phe Gly
    370                 375                 380

Leu Asp Ile Glu Ala Val Ala Ala Ala Leu Gly Val Asp Met His Thr
385                 390                 395                 400

Leu Asn Asn Met Glu Arg Thr Glu Leu Val Asn Met Leu Thr
                405                 410


<210> SEQ ID NO 10
<211> LENGTH: 410
<212> TYPE: PRT
<213> ORGANISM: Homo  sapiens

<400> SEQUENCE: 10

Leu Arg Leu His Leu Leu Leu Asn Thr Ser Val Thr Cys Asn Asp Gly
 1               5                  10                  15

Ser Pro Ala Gly Tyr Tyr Leu Lys Glu Ser Arg Gly Ser Arg Arg Trp
            20                  25                  30

Leu Leu Phe Leu Glu Ala Val Trp Tyr Cys Phe Asn Arg Glu Asn Cys
        35                  40                  45

Asp Ser Arg Tyr Asp Thr Met Arg Arg Leu Met Ser Ser Arg Asp Trp
    50                  55                  60

Pro Arg Thr Arg Thr Gly Thr Gly Ile Leu Ser Ser Gln Pro Glu Glu
65                  70                  75                  80

Asn Pro Tyr Trp Trp Asn Ala Asn Met Val Phe Ile Pro Tyr Cys Ser
                85                  90                  95

Ser Asp Val Trp Ser Gly Ala Ser Ser Lys Ser Glu Lys Asn Glu Tyr
            100                 105                 110

Ala Phe Met Gly Ala Leu Ile Ile Gln Glu Val Val Arg Glu Leu Leu
        115                 120                 125

Gly Arg Gly Leu Ser Gly Ala Lys Val Leu Leu Leu Ala Gly Ser Ser
    130                 135                 140

Ala Gly Gly Thr Gly Val Leu Leu Asn Val Asp Arg Val Ala Glu Gln
145                 150                 155                 160

Leu Glu Lys Leu Gly Tyr Pro Ala Ile Gln Val Arg Gly Leu Ala Asp
```

```
                165                 170                 175

Ser Gly Trp Phe Leu Asp Asn Lys Gln Tyr Arg His Thr Asp Cys Val
            180                 185                 190

Asp Thr Ile Thr Cys Ala Pro Thr Glu Ala Ile Arg Arg Gly Ile Arg
        195                 200                 205

Tyr Trp Asn Gly Val Val Pro Glu Arg Cys Arg Arg Gln Phe Gln Glu
    210                 215                 220

Gly Glu Glu Trp Asn Cys Phe Phe Gly Tyr Lys Val Tyr Pro Thr Leu
225                 230                 235                 240

Arg Cys Pro Val Phe Val Val Gln Trp Leu Phe Asp Glu Ala Gln Leu
                245                 250                 255

Thr Val Asp Asn Val His Leu Thr Gly Gln Pro Val Gln Glu Gly Leu
            260                 265                 270

Arg Leu Tyr Ile Gln Asn Leu Gly Arg Glu Leu Arg His Thr Leu Lys
        275                 280                 285

Asp Val Pro Ala Ser Phe Ala Pro Ala Cys Leu Ser His Glu Ile Ile
    290                 295                 300

Ile Arg Ser His Trp Thr Asp Val Gln Leu Lys Gly Thr Ser Leu Pro
305                 310                 315                 320

Arg Ala Leu His Cys Trp Asp Arg Ser Leu His Asp Ser His Lys Ala
                325                 330                 335

Ser Lys Thr Pro Leu Lys Gly Cys Pro Val His Leu Lys Gly Cys Pro
            340                 345                 350

Val His Leu Val Asp Ser Cys Pro Trp Pro His Cys Asn Pro Ser Cys
        355                 360                 365

Pro Thr Val Arg Asp Gln Phe Thr Gly Gln Glu Met Asn Val Ala Gln
    370                 375                 380

Phe Leu Met His Met Gly Phe Asp Met Gln Thr Val Ala Gln Pro Gln
385                 390                 395                 400

Gly Leu Glu Pro Ser Glu Leu Leu Gly Met
                405                 410


<210> SEQ ID NO 11
<211> LENGTH: 402
<212> TYPE: PRT
<213> ORGANISM: Homo  sapiens

<400> SEQUENCE: 11

Leu Lys Arg Val Phe Leu Ser Asn Arg Thr Val Thr Cys Asn Asp Gly
 1               5                  10                  15

Ser Gln Ala Gly Phe Tyr Leu Arg Lys Ser Pro Gly Ser Arg Arg Trp
            20                  25                  30

Val Val Phe Phe Glu Gly Gly Trp His Cys Tyr Asp His Lys Ser Cys
        35                  40                  45

Arg Ala Arg Trp Leu Lys Gln Arg His Leu Met Thr Ser Val Gln Trp
    50                  55                  60

Pro Glu Thr Arg Asp Val Gly Gly Leu Leu Ser Ala Leu Pro Ser Glu
65                  70                  75                  80

Asn Pro Tyr Trp Tyr Asn Ala Asn His Val Phe Val Pro Tyr Cys Ser
                85                  90                  95

Ser Asp Ser Trp Ser Gly Thr Lys Val Arg Pro Asp Thr Arg Asp Gly
            100                 105                 110

Leu Arg Phe Met Gly Ser Leu Ile Val Arg Gln Val Met Ser Asp Leu
        115                 120                 125

Val Pro Leu Gly Leu Gly His Ser Gln Gly Ala Asp Leu Leu Met Ala
```

```
    130                 135                 140

Gly Ser Ser Ala Gly Gly Leu Gly Val Met Leu Asn Leu Asp Lys Val
145                 150                 155                 160

Arg Thr Phe Leu Gln Asn Glu Arg Gly Leu Lys Val Ser Val Arg Gly
                165                 170                 175

Val Ser Asp Ser Gly Trp Phe Leu Asp Arg Glu Pro Tyr Thr Pro Gly
            180                 185                 190

Ala Val Ala Ala Ser Glu Ala Val Arg Gln Gly Trp Arg Met Trp Asp
        195                 200                 205

Gly Ala Leu Pro Glu Ala Cys Val Ala Glu His Ser Lys Glu Pro Trp
    210                 215                 220

Arg Cys Tyr Phe Gly His Arg Leu Tyr Asn Thr Leu Lys Ser Pro Leu
225                 230                 235                 240

Phe Val Phe Gln Trp Leu Phe Asp Glu Ala Gln Met Arg Ala Asp Ser
                245                 250                 255

Val Gly Ala Pro Val Thr Pro Gln Gln Trp Asp Tyr Ile His Asp Met
            260                 265                 270

Gly Gly Leu Arg Glu Ser Leu Asn Asn Val Ser Ala Val Phe Ala Pro
        275                 280                 285

Ser Cys Ile Gly His Ser Val Leu Thr Lys Arg Asp Trp Met Lys Ile
    290                 295                 300

Arg Ile Asp Asp Ile Thr Leu Ala Asp Ala Leu Arg Cys Trp Glu Gln
305                 310                 315                 320

Ser Asn Ala Asp Glu Arg Gln Ser Gln Trp Arg Ser Ile Asn Arg Ser
                325                 330                 335

Pro Gln Lys Leu Lys Lys Cys Ala Leu Arg Leu Leu Glu Arg Cys Ser
            340                 345                 350

Trp Pro Gln Cys Asn His Ser Cys Pro Thr Leu Thr Asn Pro Leu Thr
        355                 360                 365

Gly Glu Glu Met Lys Phe Leu Glu Leu Leu Ala Ser Phe Gly Leu Asp
    370                 375                 380

Met Asp Ala Val Ala Thr Ala Leu Gly Val Asp Met Gln Thr Leu Asn
385                 390                 395                 400

Asn Met


<210> SEQ ID NO 12
<211> LENGTH: 243
<212> TYPE: PRT
<213> ORGANISM: Homo  sapiens

<400> SEQUENCE: 12

Cys Asn Asp Gly Ser Pro Ala Gly Tyr Tyr Leu Lys Glu Ser Arg Gly
 1               5                  10                  15

Ser Arg Arg Trp Leu Leu Phe Leu Glu Ala Val Trp Tyr Cys Phe Asn
            20                  25                  30

Arg Glu Asn Cys Asp Ser Arg Tyr Asp Thr Met Arg Arg Leu Met Ser
        35                  40                  45

Ser Arg Asp Trp Pro Arg Thr Arg Thr Gly Thr Gly Ile Leu Ser Ser
    50                  55                  60

Gln Pro Glu Glu Asn Pro Tyr Trp Trp Asn Ala Asn Met Val Phe Ile
65                  70                  75                  80

Pro Tyr Cys Ser Ser Asp Val Trp Ser Gly Ala Ser Ser Lys Ser Glu
                85                  90                  95

Lys Asn Glu Tyr Ala Phe Met Gly Ala Leu Ile Ile Gln Glu Val Val
            100                 105                 110
```

```
Arg Glu Leu Leu Gly Arg Gly Leu Ser Gly Ala Lys Val Leu Leu Leu
        115                 120                 125

Ala Gly Ser Ser Ala Gly Gly Thr Gly Val Leu Leu Asn Val Asp Arg
    130                 135                 140

Val Ala Glu Gln Leu Glu Lys Leu Gly Tyr Pro Ala Ile Gln Val Arg
145                 150                 155                 160

Gly Leu Ala Asp Ser Gly Trp Phe Leu Asp Asn Lys Gln Tyr Arg His
                165                 170                 175

Thr Asp Cys Val Asp Thr Ile Thr Cys Ala Pro Thr Glu Ala Ile Arg
            180                 185                 190

Arg Gly Ile Arg Trp Asn Gly Val Val Pro Glu Arg Cys Arg Arg Gln
        195                 200                 205

Phe Gln Glu Gly Glu Glu Trp Asn Cys Phe Phe Gly Tyr Lys Val Tyr
    210                 215                 220

Pro Thr Leu Arg Cys Pro Val Phe Val Val Gln Trp Leu Phe Asp Glu
225                 230                 235                 240

Ala Gln Leu


<210> SEQ ID NO 13
<211> LENGTH: 231
<212> TYPE: PRT
<213> ORGANISM: Homo  sapiens

<400> SEQUENCE: 13

Cys Leu Asp Gly Ser Leu Pro Gly Tyr His Phe His Lys Gly Ser Gly
 1               5                  10                  15

Ser Gly Ala Asn Asn Trp Leu Ile Gln Leu Glu Gly Gly Gly Trp Cys
            20                  25                  30

Asn Asn Ile Arg Ser Cys Val Ser Arg Lys Gly Thr Arg Leu Gly Ser
        35                  40                  45

Ser Asn Phe Met Glu Lys Glu Leu Ala Phe Ser Gly Ile Leu Ser Asn
    50                  55                  60

Lys Ala Ser Glu Asn Pro Asp Phe Tyr Asn Trp Asn Arg Val Lys Val
65                  70                  75                  80

Arg Tyr Cys Asp Gly Ala Ser Phe Thr Gly Asp Ser Glu Ala Val Ala
                85                  90                  95

Pro Arg Leu Gln Phe Arg Gly Gln Arg Ile Trp Leu Ala Val Met Asp
            100                 105                 110

Glu Leu Leu Ala Lys Gly Met Arg Asn Ala Lys Gln Ala Leu Leu Ser
        115                 120                 125

Gly Cys Ser Ala Gly Gly Leu Ala Ala Ile Leu His Cys Asp Tyr Phe
    130                 135                 140

Arg Asn Leu Leu Pro Arg Thr Thr Thr Val Lys Cys Leu Ser Asp Ala
145                 150                 155                 160

Gly Tyr Phe Leu Asn Val Leu Asp Val Ser Gly Gly Pro Arg Leu Arg
                165                 170                 175

Ser Phe Phe Ser Gly Val Val Thr Leu Gln Gly Ser Ala Lys Asn Leu
            180                 185                 190

Pro Gln Ser Cys Thr Ser His Leu Lys Pro Thr Leu Cys Phe Phe Pro
        195                 200                 205

Gln Asn Val Val Ser Gln Ile Lys Thr Pro Leu Phe Leu Val Asn Ala
    210                 215                 220

Ala Tyr Asp Ser Trp Gln Ile
225                 230
```

What is claimed is:

1. An isolated polynucleotide encoding an ECA1 polypeptide comprising the sequence of SEQ ID NO. 1.

2. An isolated gene delivery vector comprising the isolated polynucleotide of claim 1.

3. An [insolated] *isolated* host cell comprising the isolated polynucleotide of claim 1.

4. A composition comprising the polynucleotide of claim 1.

5. The [insolated] *isolated* host cell of claim 3, wherein the cell is an antigen presenting cell (APC).

6. The [insolated] *isolated* host cell of claim 5, wherein the antigen presenting cell (APC) is a dendritic cell.

*7. An antibody which binds specifically to a polypeptide having the amino acid sequence of SEQ ID NO: 1.*

*8. The antibody of claim 7, wherein the antibody is selected from the group consisting of a polyclonal antibody, monoclonal antibody, Fab fragment, $F(ab')_2$ fragment, single chain antibody, chimeric antibody, and humanized antibody.*

*9. The antibody of claim 7, wherein the antibody is labeled.*

*10. The antibody of claim 9, wherein the label is a radioisotope, affinity label, enzymatic label, fluorescent label, or paramagnetic atom.*

*11. The antibody of claim 10, wherein the affinity label is biotin, avidin or streptavidin.*

*12. The antibody of claim 10, wherein the enzymatic label is horseradish peroxidase or alkaline phosphatase.*

*13. The antibody of claim 10, wherein the fluorescent label is fluorescein or rhodamine.*

*14. A composition comprising the antibody of claim 7, and a carrier therefor.*

*15. The composition of claim 14, wherein the carrier is an adjuvant.*

*16. A hybridoma which produces an antibody according to claim 7.*

*17. A method for producing an antibody that specifically binds to a polypeptide having the amino acid sequence of SEQ ID NO: 1 comprising the steps of providing an animal that is known to produce antibodies; and immunizing the animal with a polypeptide having the amino acid sequence of SEQ ID NO: 1.*

*18. The method of claim 17, further comprising the steps of removing cells from the animal's spleen; and fusing the spleen cells with myeloma cells, thereby producing hybridoma cells.*

*19. The method of claim 17, wherein the animal is a mouse or rabbit.*

*20. The method of claim 17, wherein the immunizing is performed by subcutaneous or intraperitoneal injection of the polypeptide.*

*21. The method of claim 17, wherein the polypeptide is administered with an adjuvant.*

*22. The method of claim 17, wherein the polypeptide is coupled with a heterologous protein.*

*23. The method of claim 22, wherein the heterologous protein is a globulin, β-galactosidase, or keyhole limpet cyanin.*

*24. The method of claim 18, further comprising the step of screening the hybridoma cells to identify hybridoma cells that produce antibodies specific to the polypeptide.*

*25. The method of claim 24, wherein the hybridomas are screened using an enzyme-linked immunosorbent assay, western blot analysis, or radioimmunoassay.*

* * * * *